United States Patent
Funatsu et al.

(10) Patent No.: US 7,695,958 B2
(45) Date of Patent: Apr. 13, 2010

(54) CELL-FILLED HOLLOW FIBER MEMBRANES HAVING MODIFIED CROSS-SECTION

(75) Inventors: Kazumori Funatsu, Fukuoka (JP); Kohji Nakazawa, Fukuoka (JP); Hiroshi Mizumoto, Fukuoka (JP); Junji Fukuda, Fukuoka (JP); Mikitomo Yasutake, Oita (JP)

(73) Assignee: Asahi Kasei Kuraray Medical Co., Ltd., Tokyo (JP)

( * ) Notice: Subject to any disclaimer, the term of this patent is extended or adjusted under 35 U.S.C. 154(b) by 850 days.

(21) Appl. No.: 10/525,707

(22) PCT Filed: Aug. 28, 2003

(86) PCT No.: PCT/JP03/10952

§ 371 (c)(1),
(2), (4) Date: Oct. 7, 2005

(87) PCT Pub. No.: WO2004/020614

PCT Pub. Date: Mar. 11, 2004

(65) Prior Publication Data

US 2006/0110369 A1    May 25, 2006

(30) Foreign Application Priority Data

Aug. 28, 2002  (JP)  ............................. 2002-249594

(51) Int. Cl.
*C12M 1/12* (2006.01)
*C12M 3/06* (2006.01)
*C12N 5/00* (2006.01)
*C12N 11/04* (2006.01)
*A61F 2/00* (2006.01)

(52) U.S. Cl. ................. 435/297.4; 435/182; 435/297.1; 435/400; 424/423; 424/424

(58) Field of Classification Search ....................... None
See application file for complete search history.

(56) References Cited

U.S. PATENT DOCUMENTS 6,284,451 B1 *  9/2001  Funatsu et al. ................ 435/1.1
6,802,820 B1 * 10/2004  Gorsuch et al. ............. 604/6.04

FOREIGN PATENT DOCUMENTS

| EP | 1078982 | 2/2001 |
| JP | 58-142042 | 9/1983 |
| JP | 62-171678 | 7/1987 |

OTHER PUBLICATIONS

Kazuhisa Nagata et al., "Ikei Danmen Chukushi o Riyo Shita Kansaibo Soshikitai (Organoid) Baiyoho no Kaihatsu", The Society of Chemical Engineers, Japan Dai 68 Nenkai Kenkyu Happyo Koen Yoshishu, Feb. 2003, p. 452 (L316).

* cited by examiner

*Primary Examiner*—David M Naff
(74) *Attorney, Agent, or Firm*—Young & Thompson

(57) ABSTRACT

To provide a cell-filled device that is suitable for use in, for example, an implantable or circulation type hybrid artificial organ. In a cell-filled device including hollow fiber membranes whose hollow portions are filled with cells, the hollow fiber membranes have modified cross sections, and a cell aggregate provided in each of the hollow portions has cells formed into two or more layers in arbitrary directions, provided that the distance from an arbitrary point of the cell aggregate to the nearest inner wall of hollow fiber membrane is less than 75 μm. This cell-filled device enables effective use of cells without the necrosis thereof. Further, according to the present invention, there is provided a method of manufacturing the cell-filled device.

18 Claims, 13 Drawing Sheets

CELL-FILLED HOLLOW FIBER MEMBRANES HAVING MODIFIED CROSS-SECTION

TECHNICAL FIELD

The present invention relates to a cell aggregate obtained by filling cells in modified cross-section hollow fibers, and the use and manufacturing method thereof. A cell-filled device of a modified cross-section hollow fiber membrane type of the present invention is suitably used in various applications such as an implantable or circulation type hybrid artificial organ, material production devices (e.g., bioreactors), and cell incubators (stem-cell amplifiers).

BACKGROUND ART

In recent years, as approaches for treating organs or tissues having functional failure or functional defects, the development of hybrid-type artificial organs (also referred to as biological artificial organs), and regenerative medical technologies, in which cultured cells and biocompatible materials are combined, have received much attention.

Currently, for instance, not less than 600,000 people are allegedly suffering from liver diseases in our country. In addition, about 50,000 patients have died a year because of liver diseases. Of those, about 1,000 patient deaths are due to acute liver failure and the remainder thereof is due to chronic hepatic insufficiency including hepatoma. A basic therapy for liver diseases such as hepatic insufficiency is liver transplantation. However, there is a large problem in that there is an insufficient number of offerers who are willing to donate their organs (i.e., donors). Therefore, the development of artificial livers has been demanded.

However, it is difficult to replace a total of 500 or more complicated liver functions with only an artificial means. As to an artificial liver, recently, a biological artificial liver using hepatic cells themselves has received much attention.

For the biological artificial liver, which is a representative example of a hybrid artificial organ, an extracorporeal circulation type therapeutic system is in the mainstream. The biological artificial liver carries out a therapeutic treatment by allowing a substance exchange through a plasma separator between a circuit on the body side for drawing out blood from all of the hepatic failure patients and circulating the blood and a circuit on the artificial liver module's side for carrying out a plasma circulation to metabolize and detoxify the plasma on the artificial liver module's side.

For such an artificial organ module, using dispersed cells is insufficient. That is, monolayer cultures which have been conventionally used for incubating cells cannot avoid loss or decrease of cellular functions. Thus, it is important to establish and use a multicellular aggregate body that resembles a living tissue.

From such a point of view, recently, a method of culturing an organ-like aggregate such as a spherical cell aggregate (spheroid) or a cylindrical cell aggregate (cylindroid) has been newly established, so that the high functional expression and long-term functional maintenance of cells will now be possible.

For example, as a method of culturing a spherical aggregate (spheroid), the inventors of the present invention have developed a method of forming a spheroid in a polymer base material such as a polyurethane foam (PUF) (JP10-29951A; and H. Ijima et al., "Tissue Engineering", Vol. 4, No. 2, p. 213-226 (1998)). The PUF is made of a porous material having a main framework and a thin membrane beam structure. In addition, a certain degree of passage is formed between the pores of PUF, so a high density culture can be achieved under a good environment for substance exchange. When hepatic cells are cultured in the pores of PUF, about 200 hepatic cells gradually aggregate together to form many spherical multicellular aggregates (spheroids) each having a diameter of about 100 μm spontaneously. The inventors have succeeded in developing a short-term application type (about 10 days) biological artificial liver on a human clinical scale by means of a spherical aggregate (spheroid) using this culture method.

Furthermore, the inventors of the present invention have found that hepatic cells can be introduced into hollow fibers in a very dense state by means of a centrifugal force as a result of seeking out a compact artificial liver of a long-term application type. They have finally obtained an artificial module having a cell density of $2.4 \times 10^7$ cells/$cm^3$ per module (see "Abstracts of 31st Summer Seminar Lectures in 2000 of Society of Fiber Science and Technology, Japan", p. 115-118).

Furthermore, when an improvement in operability of the artificial liver at bedside and resolving the chronic lack of donors are taken into consideration, there is a need of a more compact artificial liver capable of maintaining its functions for a long time. Therefore, the inventors of the present invention have developed a higher density of hepatic cell aggregate (hepatic cell organoid) (JP 2002-247978 A).

However, those conventional cell aggregates (organoids) have been limited to spherical one (spheroid) or cylindrical ones (cylindroids) using perfect circle-shaped hollow fiber membranes. Of those, the cell aggregate of a hollow fiber membrane type is excellent in its handling properties or functionality as a device. On the other hand, if the inner diameter of the hollow fiber membrane used is too large, sufficient amounts of oxygen and nutrients would not diffuse to the cells located at the center of the cell aggregate, causing the necrosis thereof. As a result, there were problems in that one would not be able to use the cells being filled in the hollow fiber membrane efficiently without waste. Utilization efficiency of the cells becomes an extremely large problem when a cell source for making the cell aggregate (organoid) is rarely available like one of a brain-death donor origin. In contrast, if the inner diameter of the hollow fiber membrane is too small, the manufacture of uniform hollow fiber membranes and the modularization thereof becomes difficult. Furthermore, an airlock or the like can be caused and sometimes affected the operation of uniformly filling the cells.

On the other hand, when attention is paid to the structural aspects as a substance production device, a cell culturing device of a hollow fiber membrane type is known and can be roughly classified into a type of culture cells on the internal side of a hollow fiber membrane and supplying a culture medium to the external side thereof and the opposite type. In those cases, in general, a perfect circle-shaped hollow fiber membrane has been used, but sometimes other hollow fiber membranes having a different shape than a perfect circle has been used. For instance, JP 62-171678 A discloses that cells are incubated inside or outside a modified hollow fiber membrane having a fine extending in a longitudinal direction from the outer peripheral portion thereof. In addition, JP 63-233777 A discloses that cells are incubated outside the hollow fiber membrane having unevenness in a hollow portion.

The former case has a description that the hollow fiber membrane may be oval instead of a perfect circle. However, it was the hollow fiber membrane that requires a fin (finny protrusion) on the external portion of the membrane. A main purpose of the fin is to prevent close contact between the membranes to improve the dispersibility of a culture medium and cells. In the latter case, furthermore, the inner portion of the membrane was formed with irregularity in the longitudinal direction to prevent clogging of the membrane by causing turbulence in a culture medium flowing in the membrane.

As a complex, furthermore, U.S. Pat. No. 5,015,585 discloses a hollow fiber membrane having a so-called double structure in which another hollow fiber membrane is incorporated in a hollow fiber membrane. In this case, a gap between two hollow fiber membranes is made uniform for the purpose of keeping a survival rate of the cells filled in the gap. However, in obtaining the double-structured hollow fiber membrane, it is very difficult to make the structure uniform unless the raw materials of the membrane, physical properties of the membrane, size of the module, and the like are limited. Besides, in this case, the cells cannot be expected to be filled uniformly. In terms of this fact, to a large extent, it was not practical.

In this way, various studies have been made on the shapes of cell aggregates and the hollow fiber membrane type cell culturing devices. However, no technology has attempted to increase the efficiency of using the individual cells by fully working on the cross-sectional shape and diameter of the membrane on the basis of the cell aggregate formed in the hollow fiber membrane.

DISCLOSURE OF THE INVENTION

An object of the present invention is to provide a cell-filled device of a modified cross-section hollow fiber membrane type, in which a cell aggregate is formed by filling cells in a hollow fiber, allowing efficient use of the filled cells without waste to enable an increase in utilization efficiency of cells. Another object of the present invention is to provide an artificial organ that utilizes such a cell-filled device of a modified cross-section hollow fiber membrane type. Still another object of the present invention is to provide methods of manufacturing the above device and the artificial organ.

As a result of concentrated study, the inventors of the present invention have completed the present invention by finding out that a cell aggregate (organoid) formed in a particular size by filling a modified cross-section hollow fiber with cells of interest exerts cellular functions efficiently without causing a necrotic layer in the filled cells.

That is, for achieving the above objects, the inventors of the present invention have advanced their research and development furthermore and, as a result, they have given thought to the facts that: (1) the inner diameter of the hollow fiber membrane is not restricted as far as a modified cross-section hollow fiber being deformed is used instead of the perfect circle-shaped hollow fiber membrane commonly used in the art, while a distance between the cells and the inner wall of the hollow fiber membrane is kept at a far enough distance to prevent the cells from causing necrosis; and (2) the commercially available hollow fiber membrane, which has been known to be made of many different materials and to have permeating properties, can be used when the modified cross sections as mentioned above is made by deforming the perfect circle-shaped hollow fiber membrane. Furthermore, the inventors of the present invention have given thought to the facts that the affinity between the cells and the membrane and the substance permeability of the cell-filled device of a modified cross-section hollow fiber membrane type can be designed without restriction, so the device can find use in a remarkably increased number of applications including implantable and circulation type hybrid artificial organs. No reports have been conventionally made on cell aggregates (organoids) each using such a modified cross section hollow fiber.

The present invention pertains to the following (1) to (29).

(1) A cell-filled device of a modified cross-section hollow fiber membrane type, including hollow fiber membranes whose hollow portions are filled with cells, characterized in that:

the hollow fiber membranes have modified cross sections; and a cell aggregate provided in each of the hollow portions has cells formed into two or more layers in arbitrary directions, provided that a distance from an arbitrary point of the cell aggregate to the nearest inner wall of the hollow fiber membrane is less than 75 µm.

(2) The cell-filled device of a modified cross-section hollow fiber membrane type according to (1), in which the distance to the nearest inner wall of the hollow fiber membrane is 50 µm or less.

(3) The cell-filled device of a modified cross-section hollow fiber membrane type according to (1) or (2), characterized in that a cross-section of the modified cross-section hollow fiber membrane is in a flat form.

(4) The cell-filled device of a modified cross-section hollow fiber membrane type according to any one of (1) to (3), characterized in that a pore size of the hollow fiber membrane is 0.001 to 5 µm.

(5) The cell-filled device of a modified cross-section hollow fiber membrane type according to (4), characterized in that the pore size is 0.05 to 1 µm.

(6) The cell-filled device of a modified cross-section hollow fiber membrane type according to any one of (1) to (5), characterized in that the hollow fiber membrane is made of a synthetic polymer having a contact angle of 70 degrees or less.

(7) The cell-filled device of a modified cross-section hollow fiber membrane type according to (6), in which the synthetic polymer is a thermoplastic resin.

(8) The cell-filled device of a modified cross-section hollow fiber membrane type according to (7), in which the thermoplastic resin is a polyethylene-based resin.

(9) The cell-filled device of a modified cross-section hollow fiber membrane type according to any one of (1) to (8), characterized in that at least an inner surface of the hollow fiber membrane contains a hydrophilic polymer.

(10) The cell-filled device of a modified cross-section hollow fiber membrane type according to any one of (1) to (9), characterized in that the cells are cells derived from an animal tissue.

(11) The cell-filled device of a modified cross-section hollow fiber membrane type according to (10), characterized in that the cells derived from an animal tissue are at least one kind of cell selected from the group consisting of cells derived from a liver, cells derived from a spleen, stem and precursor cells thereof, and genetic recombinant cells.

(12) The cell-filled device of a modified cross-section hollow fiber membrane type according to (11), characterized in that the cells derived from an animal tissue are hepatic cells.

(13) The cell-filled device of a modified cross-section hollow fiber membrane type according to any one of (10) to (12), characterized in that the cells derived from an animal tissue are cells derived from a human organ.

(14) A cell-filled device, including hollow fiber membranes and cells, the device being provided as the cell-filled device of a modified cross-section hollow fiber membrane type for implantation according to any one of (1) to (13), in which each of the hollow portions contains a cell aggregate and both ends of each hollow fiber membrane are sealed.

(15) A cell-filled device of a modified cross-section hollow fiber membrane type for a hybrid artificial organ, which is one according to any one of (1) to (13).

(16) A hybrid artificial organ, including at least one cell-filled device of a modified cross-section hollow fiber membrane type according to any one of (1) to (13).

(17) A hybrid artificial organ, including at least one cell-filled device of a modified cross-section hollow fiber membrane type according to any one of (1) to (13), being housed in a container having an inlet and an outlet for a liquid to be treated, characterized in that an inside of a hollow of the cell-filled device of a modified cross-section hollow fiber membrane type is separated from an external of the hollow forming a communication path of the liquid to be treated.

(18) A method of manufacturing a cell-filled device of a modified cross-section hollow fiber membrane type, including the steps of:
  a) obtaining a modified cross-section hollow fiber membrane; and
  b) injecting a cell suspension into a hollow of the hollow fiber membrane.

(19) The method of manufacturing a cell-filled device of a modified cross-section hollow fiber membrane type according to (18), further including the step of producing the hollow fiber membrane using double annular spinning nozzle having a modified cross section.

(20) The method of manufacturing a cell-filled device of a modified cross-section hollow fiber membrane type according to (18), further including the step of applying an external force for deformation to a hollow fiber membrane not having a shape of interest in an approximately vertical direction of its fiber axis to obtain the modified cross-section hollow fiber membrane.

(21) The method of manufacturing a cell-filled device of a modified cross-section hollow fiber membrane type according to (18), further including the step of drafting the hollow fiber membrane not having a shape of interest in the direction of its fiber axis while deforming the shape of the cross section to mold the membrane into the modified cross-section hollow fiber membrane.

(22) The method of manufacturing a cell-filled device of a modified cross-section hollow fiber membrane type according to any one of (18) to (21), characterized in that the cross section of the modified cross-section hollow fiber membrane is in a flat form.

(23) The method of manufacturing a cell-filled device of a modified cross-section hollow fiber membrane type according to any one of (18) to (22), characterized in that a material of the hollow fiber membrane is a thermoplastic resin.

(24) The method of manufacturing a cell-filled device of a modified cross-section hollow fiber membrane type according to any one of (18) to (23), characterized in that injected cells are cells derived from an animal tissue.

(25) The method of manufacturing a cell-filled device of a modified cross-section hollow fiber membrane type according to (24), characterized in that the cells derived from an animal tissue are at least one kind of cell selected from the group consisting of cells derived from a liver, cells derived from a spleen, stem and precursor cells thereof, and genetic recombinant cells.

(26) The method of manufacturing a cell-filled device of a modified cross-section hollow fiber membrane type according to (25), characterized in that the cells derived from an animal tissue are hepatic cells.

(27) The method of manufacturing a cell-filled device of a modified cross-section hollow fiber membrane type according to any one of (24) to (26), characterized in that the cells derived from an animal tissue are cells derived from a human organ.

(28) A method of manufacturing a hybrid artificial organ including the method of manufacturing a cell-filled device according to any one of (18) to (27).

(29) A method of manufacturing a hybrid artificial organ characterized in that:
  at least one modified cross-section hollow fiber membrane used in the method of manufacturing a cell-filled device according to any one of (18) to (27) is housed in a container having an inlet and an outlet for a liquid to be treated, and an injection opening for cells; and
  potting is performed such that an inside of a hollow is communicated with the injection opening for cells and separated from an external portion of the hollow, followed by injecting cells into hollow portions to form a cell aggregate.

According to the present invention, the device can function efficiently as a hybrid artificial organ because cells filled in the modified cross-section hollow fiber function efficiently without waste and without causing any necrotized layer.

BEST MODE FOR CARRYING OUT THE INVENTION

Hereinafter, the present invention will be described in detail.

Figure 1:
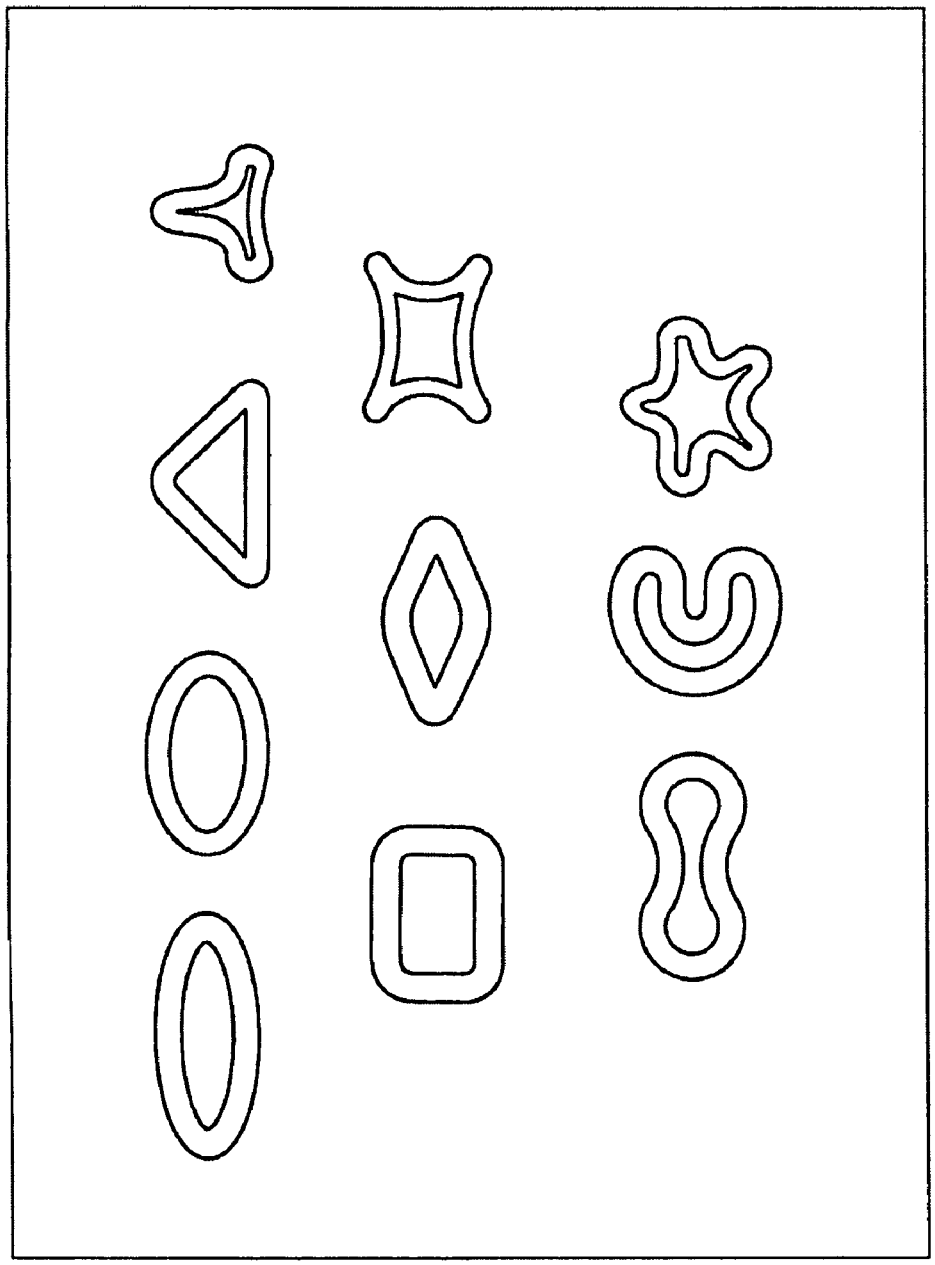
FIG. 1 is a schematic diagram showing the cross section of a modified cross-section hollow fiber membrane of the present invention.

The modified cross-section hollow fiber membrane of the present invention is not intended for a cross-sectional structure generally used for a blood purifying membrane, a ultra filtration membrane, or the like and having inner and outer peripheral portions which are in the shapes of perfect circles and arranged concentrically. In this case, however, the cross-sectional structure of at least an inside of the hollow fiber membrane is intentionally deformed particularly in order to define a distance from the arbitrary point of the cell aggregate (organoid) formed in the hollow portion to the nearest inner wall of a hollow fiber membrane within a specific range. As shown in FIG. 1, specific examples of the shape include a flat shape, an oval shape, polygonal shapes such as triangle, quadrangle, and pentagonal forms, and infinite forms such as comma-shaped bead and star forms. Of those, in consideration of the easiness of filling with the cells and the handling of the membrane, the flat or oval shape is preferable. The flat shape is particularly preferable.

The modified cross-section hollow fiber membrane is preferably designed such that the forms of inner and outer peripheral portions are almost equal and concentric with each other (in other words, the membrane thickness thereof is almost uniform). For any purpose, the inner and outer peripheral portions may have different forms.

The term "modified cross section" used herein represents the shape of a cross section obtained by cutting the hollow fiber membrane in the axial direction of the fiber. For instance, the shape of a cross section modified in the axial direction of the fiber, which is described in the prior art (JP 63-233777 A) is also out of category. This is because such a shape does not attain the object of keeping a space between the cells and the inner wall of the hollow fiber membrane of the present invention at a distance far enough to prevent the cells from causing necrosis thereof, is hardly formed uniformly, and hardly permits the filling of cells.

As a structure of a membrane portion, the modified cross-section hollow fiber membrane may use any conventionally known hollow fiber membrane structures such as a sponge structure, a uniform structure, and a macrovoid structure. In addition, the structure of the modified hollow fiber may be straightened out in the axial direction of the fiber, or crimped in waves.

Preferably, the material of the modified cross-section hollow fiber membrane used in the present invention is a thermoplastic resin from the viewpoint of the deforming process described later. Examples of the material include polyolefin-based, polyester-based, polysulfone-based, polyethersulfone-based, polypropylene-based, polyethylene-based, polyacrylonitrile-based, polymethylmethacrylate-based, polyvinyl chloride-based, and polyamide-based resins. The reason of describing those materials as "- - - based" is that the polymer mentioned above may be provided as a main component and, for any purpose, a secondary component may be blended or introduced by graft polymerization. Alternatively, the secondary component may be any copolymer including random and block copolymers.

The modified cross-section hollow fiber membrane used in the present invention is made of the thermoplastic resin described above, preferably a synthetic polymer having a contact angle of 70 degrees or less. Here, the term "contact angle" of the synthetic polymer is defined as follows. That is, a synthetic polymer is uniformly applied on a support in a horizontal position such as a uniform film made of a synthetic polymer or a glass plate, and then dried to obtain a product. Then, pure water is dropped on the product to form a liquid droplet. At this time, the contact angle is an angle on the liquid-including side among angles that a flat surface makes with a tangent at a contact point among three phases, liquid droplet, synthetic polymer surface, and gas phases, which is a tangent to the liquid.

Making the hollow fiber membrane of such a synthetic polymer is preferable because, in particular, the cells can be prevented from attaching on the inner surface at some degree and a decrease in substance permeability of the membrane due to the cellular attachment can be reduced. In addition, it is also preferable in terms of a substance exchange through the membrane because of an improvement in wettability of the hollow fiber membrane with the liquid to be treated, such as blood, plasma, or a physiological solution.

The synthetic polymer that satisfies a contact angle of 70 degrees or less can be suitably selected from the thermoplastic resins described above or may be one obtained by applying the thermoplastic resin described above on a membrane made of any material.

In the present invention, at least an inner surface of each of those modified cross-section hollow fiber membranes, or a contact surface with at least cells may contain a hydrophilic polymer for the purpose of controlling the affinity for cells.

Examples of the hydrophilic polymer include: hydrophilic synthetic polymers such as polyethylene glycol, polyvinyl alcohol, polyvinyl pyrrolidone, ethylene-vinyl alcohol copolymer, polyethylene imine, and polyallyl amine; and hydrophilic polysaccharides such as cellulose, chitosan, agarose, dextran, and dextran sulfate. However, the polymer is not limited to those polymers. Any polymer may be used as long as it is capable of controlling the viability of the cells being attached.

Of those, exceptionally preferable is the ethylene-vinyl alcohol copolymer. According to the findings of the inventors of the present invention, the ethylene-vinyl alcohol copolymer shows a high rate of the organoid formation of hepatic cells at an early stage, while showing a low enough cellular attachment property to prevent the loss of substance permeability of the membrane.

Any of those hydrophilic polymers may be introduced into at least an inner surface of the modified cross-section hollow fiber membrane by means of any of blending, graft polymerization, copolymerization, or the like as well as coating. Of course, it may be introduced into the entire membrane.

For the substance permeability of the modified cross-section hollow fiber membrane, a pore size may be as large as possible in terms of a mass transfer. In consideration of the leakage of cells, the pore size may be small. For satisfying both points, the pore size is in the range of 0.001 to 5 μm, which can be suitably selected on the basis of the molecular weight of the material and the size of cells for the purpose of detoxification or removal. In consideration of the supply of a culture solution containing various nutritive substances, i.e., permeability of water and nutrients, the pore size is preferably in the range of 0.05 to 1 μm.

The cell-filled device of a hollow fiber membrane type of the present invention is obtained by: filling the inside of the hollow portion of the modified cross-section hollow fiber membrane with cells; and then aggregating the cells to provide a cell aggregate (organoid). For retaining the cells to be utilized in the hollow portion, there is a need for a means of injecting cells. However, the form and mechanism thereof are not particularly limited, as will be described in a manufacturing method later. Thus, those matters may be appropriately chosen and used.

The term "cell aggregate" (organoid) as used herein is a multicellular aggregate made of cells being accumulated, which approximates an organ having functions originally found in the cellular tissue. For instance, a multicellular aggregate made of hepatic cells being accumulated, which are obtained in the present invention, can be referred to as a cell aggregate (organoid) because it exhibits hepatic functions such as an ammonia removal effect and an albumin secretion effect, which are inherent functions of the liver tissue. The cell aggregate (organoid) as used herein is not limited to a cell aggregate formed by filling and densifying the cells by means of a dynamical procedure such as centrifugal forces or pressure as defined in JP 2002-182677 A. For instance, as disclosed in JP 10-33671 A, there is also a cell aggregate formed by: filling hepatic cells in an inner cavity of a hollow fiber; incubating the resultant in a perfusion solution; growing the hepatic cells in the inner cavity of the hollow fiber to produce an extracellular matrix; and then proceeding cell-cell adhesion and intercellular matrix-cell adhesion.

The cells used in the present invention are cells derived from the tissue of an animal. Depending on the collection portion, examples of the cells include: organ-derived cells such as cells derived from the liver (containing at least one of hepatic cells, endothelial cells, Kupffer cells, and fibroblast cells), cells derived from the spleen, heart muscle cells, cells derived from the kidneys; and tissue cells such as skin cells, epidermal keratinocytes, fibroblast cells, vascular endothelial cells, vascular wall cells, nerve cells, and cartilage cells. Those cells may be combined with each other to use. In addition, depending on the development stage, in addition to those mature cells, stem cells or precursor cells may be used. Furthermore, for the normal cells, genetic recombinant cells may be used. Examples of genetic recombinant cells include cells being immortalized by the introduction of immortalizing genes such as Tert, Bmi1, Large T of SV40, and Bc12.

Of those, the cells used in the cell-filled device of a modified cross-section hollow fiber membrane type of the present invention are most preferably hepatic cells. The liver is one of the larger organs. The liver has a wide variety of complicated functions. For example, the liver relates to by the synthesis, or storage of materials required for the living body, such as proteins and sugars, or metabolic detoxication for ammonia, drugs, or the like, and the digestion of fat and the absorption of vitamins by the release as an external secretory organ of bile acid or the like. Therefore, the device using hepatic cells can be very useful in terms of functions in spite of being small.

The cell sources of the present invention include normal hepatic cells derived from laboratory mice, rats, guinea pigs, rabbits, dogs, pigs, baboons, and humans but not limited to these sources. The established hepatic cells may be also provided as targets.

In the case of normal hepatic cells, isolated hepatic cells can be obtained using a general enzymatic digestion method by which the liver is treated with an enzyme solution such as a collagenase solution.

The cell density filled in the modified cross-section hollow fiber membrane is preferably $1 \times 10^7$ cells/cm$^3$ or more. When the cell density is equal to or more than that, the device can be compacted when it is used as the implantable or circulation type hybrid artificial organ.

By the way, when the cells are hepatic cells in particular, the cell density is preferably more than $5 \times 10^7$ cells/cm$^3$. The cell density in the living human liver is 1 to $2 \times 10^8$ cells/cm$^3$. Thus, it is desired that the cell density of the hepatic cell aggregate (organoid) be close to the cell density of the living liver. In addition, when the cells are filled at high density by means of centrifugal forces and hydrostatic pressures, the filling can be attained as the load thereof is high. However, when the load is too high, the hepatic cells themselves will receive damage or die, so the functions of the hepatic cells cannot be kept. Therefore, in the case of the hepatic cell aggregate (organoid), the density of the cells is more than $5 \times 10^7$ cells/cm$^3$ but not more than $2 \times 10^8$ cells/cm$^3$, preferably $8 \times 10^7$ cells/cm$^3$ or more, more preferably $9 \times 10^7$ cells/cm$^3$ or more.

The cell aggregate (organoid) of the present invention should be composed of two or more layers of cells being accumulated in arbitrary directions. As long as the cell aggregate has a thickness corresponding to the two or more layers, the functions of the cell aggregate (organoid) can be exerted. The term "two or more layers of cells being accumulated in arbitrary directions" as used herein means that the cells are accumulated to form two or more layers even though the cell aggregate (organoid) is cut any radial direction. The term "a distance from an arbitrary point of the cell aggregate to the nearest inner wall of the hollow fiber membrane is less than 75 μm" means that a distance from any point of the cell aggregate (organoid) formed in the hollow portion to the inner wall of the hollow portion cannot be 75 μm or more. If it becomes 75 μm or more, the supply of oxygen cannot reach the cells located in the center of the cell aggregate(organoid), thereby causing necrosis. Therefore, the thickness of the cell aggregate (organoid) in the present invention should correspond to two or more layers. In addition, a distance from any point of the cell aggregate (organoid) formed in the hollow portion to the inner wall of the nearest hollow fiber should be less than 75 μm. Here, the term "thickness" means a thickness from the surface layer of the cell aggregate (organoid) to the opposite of the surface of the cell aggregate. A thickness (length) of the cell aggregate (organoid) formed in the modified hollow fiber membrane can be appropriately set in the axis direction of its fiber. In addition, when the modified hollow fiber membrane is in a flat form, for example, the thickness in the major axis direction is defined at will as far as the thickness in the minor axis direction satisfies the above description.

When the cell aggregate (organoid) has a higher cell density, the gaps between cell to cell decreases. Thus, the thickness cannot be increased substantially because of the need for supplying oxygen. On the other hand, even though the cell density is within the range of the present invention, a larger thickness is preferable when the cell density is comparatively small. Therefore, in the cell aggregate (organoid) of the present invention, it is more preferable to establish a reversed correlation between the cell density and the thickness.

In the cell aggregate (organoid) of the present invention, except the surface thereof, it is important that the respective cells contact each other in a three-dimensional perspective manner. In the living liver, it has been recognized that hepatic cells express the functions thereof by exchanging information between the adjacent cells through various cell-cell connections. In the present invention, the hepatic cells are subjected to physical forces such as centrifugal forces and hydrostatic pressures when filled at high density. Therefore, a tissue-like body having a high cell density can be formed by considerably improving the frequency of contact between the cells.

It has been also possible to form a cell aggregate by filling the cells in the inner cavity of the hollow fiber and then growing the cells to make the cells be in close contact with each other.

In addition, the cell aggregate (organoid) of the present invention is preferably provided with a skin layer on the surface of the accumulated body thereof. When the hepatic cells are subjected to physical forces such as centrifugal forces and hydrostatic pressures, and then incubated for 3 to 5 days, the cells on the surface layer of the cell aggregate (organoid) become flattened and the surface layer of the cell aggregate (organoid) becomes smooth, causing the emergence of a skin layer. The skin layer may be caused by the cellular state of the surface layer of the cell aggregate (organoid) and a cellular secretion product.

Next, a hybrid artificial organ using the cell-filled device of a modified cross-section hollow fiber membrane type will be described.

Figure 12:
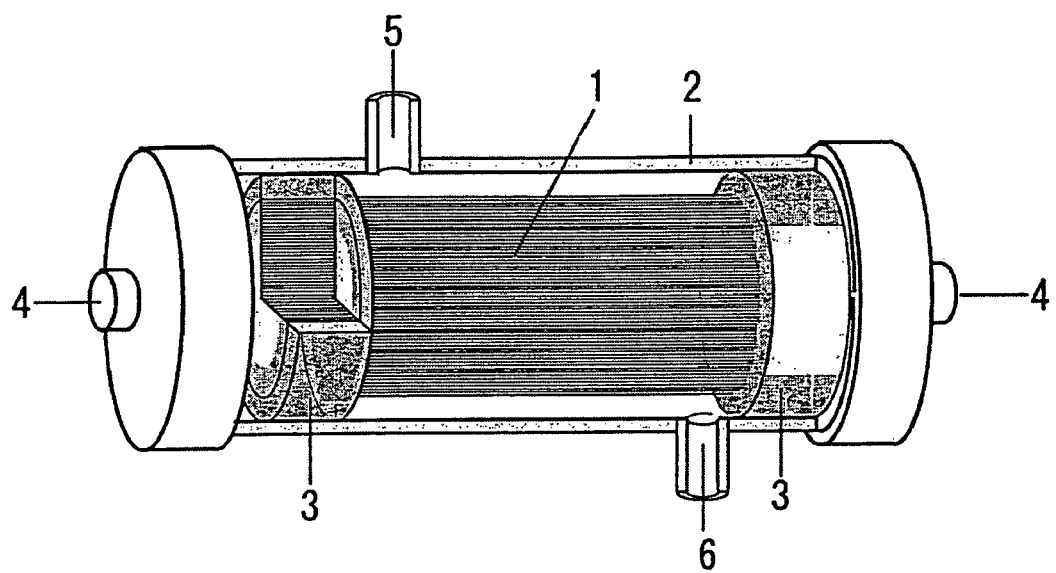
FIG. 12 is a schematic diagram showing a hybrid artificial organ of the present invention.
Figure 13:
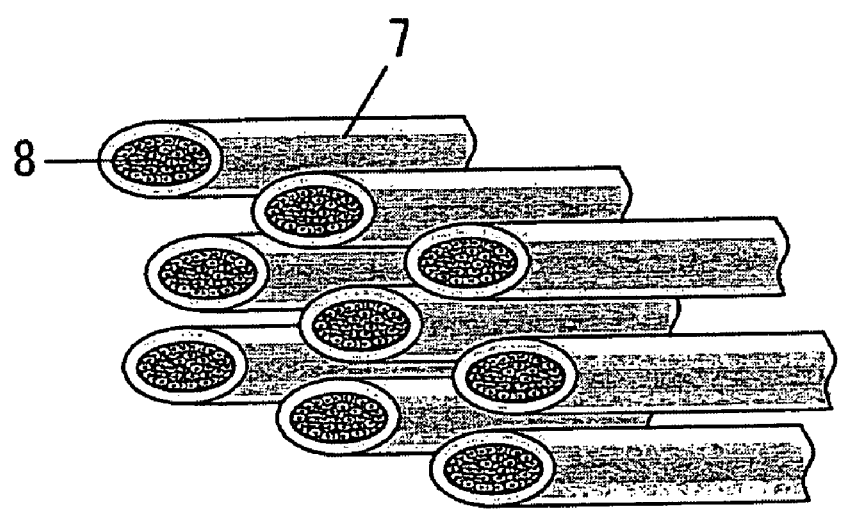
FIG. 13 is a schematic diagram showing a state where cells are filled and immobilized in a modified cross-section hollow fiber membrane installed in the hybrid artificial organ of the present invention.

In a module obtained such that at least one of the modified cross-section hollow fiber membranes of the present invention is housed in a container having an inlet and an outlet for a culture medium or a liquid to be treated, and an injection opening for cells, and in addition, the inside of the hollow is communicated with the injection opening for cells, and furthermore, the inside of the hollow is potted so as to be separated from the external portion of the hollow that forms a passage of the liquid to be treated. Therefore, a cell aggregate (organoid) formed by filling the cells to be utilized into the hollow portion of the hollow fiber membrane will be used as a hybrid artificial organ. FIG. 12 and FIG. 13 show schematic diagrams of a hybrid artificial organ of the present invention, in which a modified cross-section hollow fiber is incorporated.

As shown in FIG. 12, a container 2 having an inlet and an outlet (5 and 6) for a culture solution or a liquid to be treated has at least one modified cross-section hollow fiber membrane 1 being filled. Both ends of the modified cross-section hollow fiber membrane are subjected to a potting process and fixed such that the inside of the hollow is communicated with the injection opening for cells in sealing portions 3, while being separated from the external portion of the hollow forming a passage for the liquid to be treated.

For the container and potting structure, any of container materials and shapes generally used for hollow fiber membrane type blood purifiers is available. For instance, a suitable container material is one having high strength and high transparency and provides excellent safety, which is typified by a polycarbonate-based resin or a polystyrene-based resin. Additionally, but not particularly limited to, a cheap polyolefin-based resin or any of various copolymer resins may be used. In addition, the container may be shaped such that a body portion is cylindrical and a flow channel of the liquid to be treated is provided in the vicinity of both ends thereof. In the container, at least one cell-filled device of a modified cross-section hollow fiber membrane type of the present invention is installed.

Furthermore, the potting structure is not particularly limited, and may have any of configurations. For instance, like a hollow fiber membrane type blood purifier, the potting structure may be one in which both ends of the hollow fiber membrane in the container are potted and then the inner and outer sides of the membrane are separated from each other. Alternatively, like an example of an endotoxin cut filter, both ends thereof are potted or one of the ends is provided as a sealed end. Furthermore, alternatively, like an example of a house-hold water purifier of a hollow fiber membrane type, the hollow fiber membrane is installed in the container in the shape of letter U and one end thereof is potted.

The above module is provided with at least one injection opening 4 for cells to introduce cells into the module in addition to the inlet and outlet (5 and 6) for a culture solution or a liquid to be treated. Thus, a cellular suspension is introduced from the injection opening 4 for cells and then introduced into the hollow portion of each of the hollow fiber membranes through an opening end of the hollow fiber membrane at the sealing portion 3. Another sealing portion 3 on the opposite end may be provided such that the opening end of the hollow fiber membrane is sealed in advance or sealed after the introduction of cells. As described above, after the cells are introduced into the hollow portion of the hollow fiber opening end, the cells can be immobilized in the hollow portion by sealing the sealing portion 3 on the cell injection side with a treatment of sealing the injection opening 4 for cells, or the like. The resultant is a so-called hybrid artificial organ in the present invention. The appearance of cells immobilized in the hollow portion is schematically shown in FIG. 13.

In this module, in the container 2, a culture solution flows in a space formed between the external side of the hollow fiber membrane and the sealing portion through the culture medium inlet 5 and the culture medium outlet 6. Here, the culture solution, which is filled in the inside of the modified cross-section, is used for supplying oxygen and nutrients to cells forming the cell aggregate (organoid) and for the removal of a metabolic decomposition product. In this space, furthermore, blood, plasma, a diluent thereof, or a blood preparation, provided as a liquid to be treated, may flow.

The hybrid artificial organ having a container structure as described above has a modified cross-section hollow fiber membrane as an installed hollow fiber membrane. Thus, the liquid to be treated tends to uniformly flow in the space between the membranes. In addition, it is excellent in the efficiency of substance exchanges such as detoxification and removal. Besides, it is suitable for a hybrid artificial organ capable of maintaining the functions for a long time. In addition, the hybrid artificial organ can be also obtained by appropriately deforming a hollow fiber membrane commercially available. Consequently, there is an advantage of utilizing cell aggregates (organoid) filled in membranes made of various materials and having substance permeability.

Next, a method of manufacturing a cell-filled device of a modified cross-section hollow fiber membrane type of the present invention will be described.

For manufacturing the cell-filled device of a modified cross-section hollow fiber membrane type of the present invention, at first, a step of obtaining a modified cross-section hollow fiber membrane is needed.

The modified cross-section hollow fiber membrane of the present invention can be prepared using any of the fiber-spinning methods known in the art, such as a wet process, drying process, and a melting process. However, a method may be appropriately selected so as to be suitable for the membrane materials used.

Figure 2:
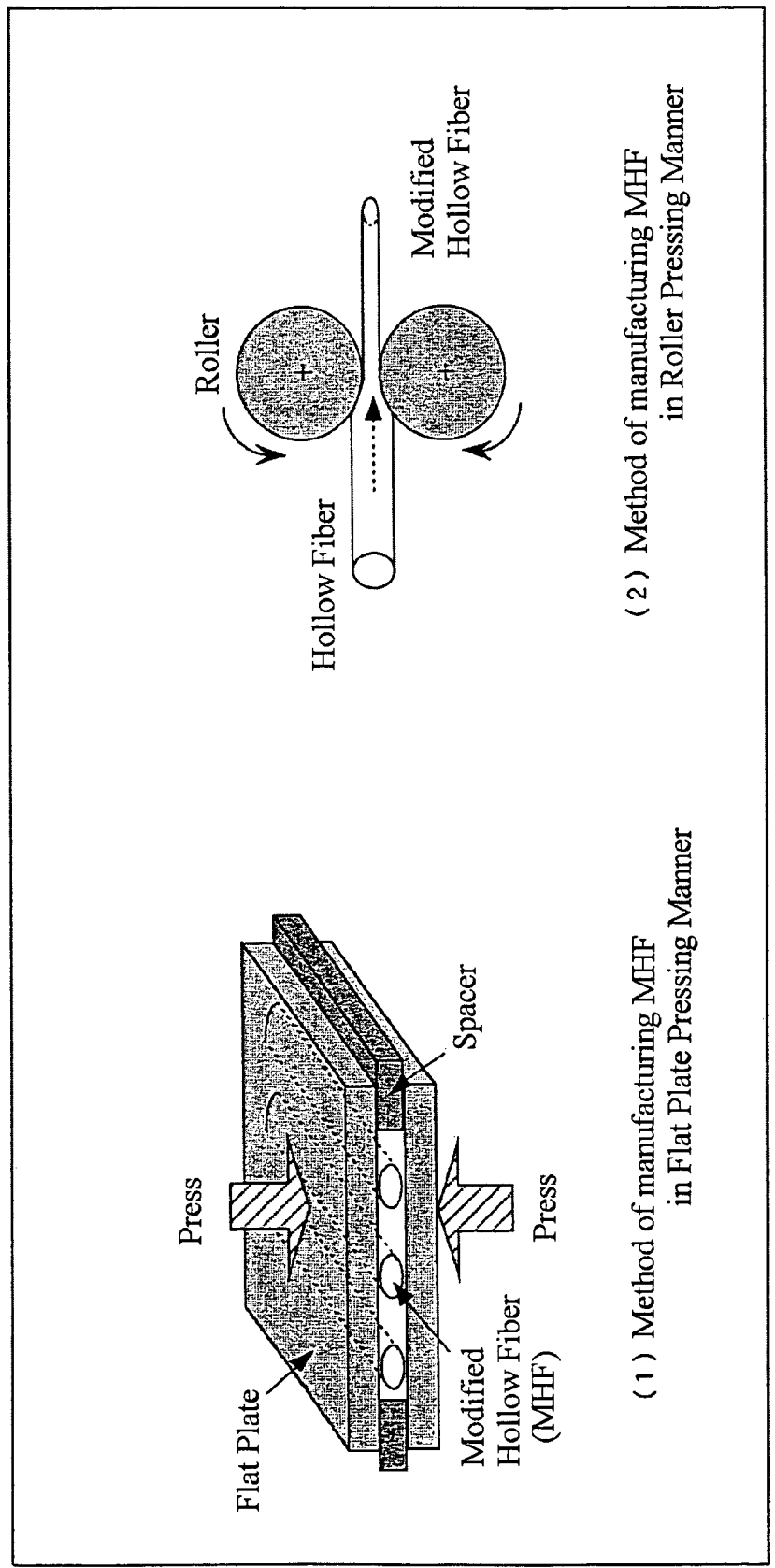
FIG. 2 is a schematic diagram showing a manufacturing method of the modified cross-section hollow fiber membrane of the present invention.

The methods of obtaining the modified cross-section hollow fiber membrane include a method for the formation of a modified cross section simultaneously with the membrane formation and a method for deforming a hollow fiber membrane by subjecting the hollow fiber membrane to a mechanical processing after membrane formation. In the former, a spinning solution may be discharged from a double annular spinning nozzle having a modified cross section and then coagulated. The former is preferable because modified cross-section hollow fiber membranes of various shapes can be obtained by using a spinning nozzle having a cross sectional shape of interest. In addition, in the latter, a hollow fiber membrane that has already been formed may be subjected to a deforming force from the substantially vertical direction of the fiber axis. For example, as shown in FIG. 2, the hollow fiber membrane can be cut into appropriate lengths and deformed using a pressing machine having a specific shape. Alternatively, a slit roller having a constant width and a specific form designed to sandwich a hollow fiber membrane is preferably used because the hollow fiber membrane can be continuously deformed during the fiber-forming step or after the membrane-forming. Such a deforming process after the membrane formation can utilize any commercially available hollow fiber membranes. Thus, even though the inner diameter of the hollow fiber member is so large that it is inherently unstable to the organoid, it can be deformed into desired dimensions by means of flattening or the like. Besides, it is very preferable in that the advantages of membrane materials and substance permeability can be used effectively. In any case, when an external deforming force is applied, a thermal setting may be preferably applied at temperatures which do not deform the membrane material.

By the way, in particular, a melt spinning method using a polyolefin-based resin or a polyethylene-based resin may deform (flatten) the shape of the cross section simultaneously by drafting the hollow fiber membrane in the axial direction of the fiber using a drawing roller having a hardened surface in a drawing treatment which is generally carried out in the art. This is because the rate of solidification of the spinning solution is slow in melt spinning in comparison with wet spinning, so the membrane during the membrane formation can be easily deformed. Such a method is particularly preferable because a specific spinning nozzle and post processing are not needed.

Next, there is a need for a step of injecting a cell suspension into the hollow portion of the modified cross-section hollow fiber membrane. In this step, it is desired to provide means for injecting cells for intensed use into the hollow portion of the hollow fiber membrane in advance. For instance, at least one end of the hollow fiber membrane is subjected to a resin potting process and then hardened, followed by cutting the resin so as to form an open end of the hollow fiber membrane. After the other end is sealed, the opening end may be provided with a fixture, nozzle, or the like for injecting a cell suspension into the opening end. However, the sealing means, injection fixture, and so on are not particularly limited.

For obtaining the hybrid artificial organ by filling and immobilizing cells after housing the modified cross-section hollow fiber membrane in the container, the resulting modified cross-section hollow fiber membrane is installed in a cylindrical container having an inlet and an outlet for a culture solution or a liquid to be treated and then at least one end thereof is potted. As exemplified previously, the potting form is not particularly limited. Potting may be performed on both ends or may be performed on one end mounted with a U-shaped hollow fiber membrane, which may be separated so as to prevent a short pass inside and outside the hollow membrane members. Next, after the potting resin is hardened, the end of the resin is cut to form an opening end of the modified cross-section hollow fiber, followed by mounting a header cap having an injection opening for cells. A series of molding methods may be carried out on the basis of a method of molding a well known blood purifier, water purifier, or the like of a hollow fiber membrane type, and is not particularly limited. In this case, before the injection of cells, an opening end or a header nozzle opposite to the injection opening for cells is sealed to prevent the injected cells from flowing out.

Subsequently, when the cell suspension is injected into the hollow portion of the hollow fiber membrane, cells being dispersed are subjected to external forces such as centrifugal forces and hydrostatic pressures to allow a liquid element to be removed through filtration while filling a high cell density for incubation. Concretely, the cells are placed in the hollow fiber and then packed at high density by an effect of physical forces such as centrifugal forces and hydrostatic pressures. In the case of a method of loading with centrifugal forces, the cells are accumulated at high density and then incubated for a predetermined time to obtain the cell aggregate (organoid). Similarly, in the case of a method of loading with hydrostatic pressures, the cells are loaded with the hydrostatic pressures and incubated to obtain the cell aggregate (organoid). Alternatively, hepatic cells are filled in the inner cavity of the hollow fiber to grow hepatic cells by means of a perfusion and to produce an intracellular matrix. Furthermore, the cell-cell adhesion or the cell-intercellular matrix adhesion can be proceeded to obtain a cell aggregate.

It is preferable to prepare a cell suspension before injection into the hollow fiber in order to prevent damage to the cells. For attaining a high density without damaging the cells, the concentration of the cell suspension is preferably $2 \times 10^7$ cells/ml or less, more preferably 0.1 to $1 \times 10^7$ cells/ml. For filling at high density, it is preferable to perform the injection while removing only the culture solution from a pore of the hollow fiber membrane.

After the cells are injected into the hollow portion of the hollow fiber membrane, in substantially the axial direction of the hollow fiber membrane, a centrifugal force of 5 to 1,500 G is applied for about 30 to 600 seconds to accumulate the cells at high density. If the centrifugal force exceeds 1,500 G, the cells will be damaged or killed. For preventing the cells from being killed, a suitable centrifugal force may correspond to a load of about 60 G×90 seconds.

In the case of using hydrostatic pressure, the hollow fiber injected with cells is set up and then a hydrostatic pressure of 5 to 25 kPa is loaded in the hollow fiber for 4 to 120 hours. Most preferable is to load with a constant hydrostatic pressure of 10 kPa for 24 hours.

The cells are filled as described above and then the cell aggregate (organoid) is formed by incubating the cells, resulting in a cell-filled device of the present invention.

The culture solution used may be a serum-free medium prepared by adding hormones and inorganic salts to a basic medium such as William E Medium (WE) or Dulbecco's Modified Eagle Medium (DMEM) or a serum-containing medium prepared by adding serum to the basic culture of WE, DMEM, or the like.

As described above, in the present invention, the immobilized cell-filled device having cells filled in the modified cross-section hollow fiber membrane is effectively used as a hybrid artificial organ being modularized and installed in the container.

Furthermore, for instance, a hollow fiber membrane portion is collected from the modified cross-section hollow fiber membrane or the hybrid artificial organ after the formation of a cell aggregate (organoid) and then both ends thereof are sealed with a procedure so as to prevent cells from leaking. The resultant can also be suitably used.

The sealing form of the hollow fiber membrane is not particularly limited as long as the cells being filled are not leaked from the opening portion of the membrane. For instance, several-millimeter to several-centimeter parts of both ends of the hollow fiber membrane may be pressed, bent, thermally welded, embedded with a potting material, or the like. In particular, it is more preferable that the hollow fiber membrane be made a biodegradable polymer known in the art because it can be used as an implant use type device.

The cell-filled device of a modified cross-section hollow fiber membrane type having such a sealing structure and composed of the hollow fiber membrane and cells is also favorably used as a device for an artificial organ capable of maintaining its functions for a long time. In addition, the device can be attained by suitably deforming a commercially available hollow fiber membrane. Thus, there is an advantage in that the cell aggregate (organoid) filled in the membrane made of any of various materials and having substance permeability can be used.

EXAMPLES

Hereinafter, the present invention is more specifically described with reference to examples, but the present invention is not limited to them.

The preparation of hepatic cells used for forming a cell aggregate (organoid) in the present invention as well as the measurement of the functional activity of the resulting hepatic cell aggregate (organoid) were performed as follows.

(Preparation of Hepatic Cells)

For preparing primary rat hepatic cells, 150 ml of a solution of 0.5 mg/ml collagenase (manufactured by Wako Pure Chemical Industries, Ltd.) was prepared. After a cannula was introduced into the portal vein (the blood vessel which leads to the liver) of a male Wistar-line rat at 7 weeks of age (weight: 250 g) and the blood was drawn for 5 minutes at 30 ml/min, the collagenase solution heated to 37° C. was fed thereinto for 10 minutes at 15 ml/min. The liver treated with collagenase was put into a culture solution and the hepatic cells were dispersed using a scalpel and a pipette. The resulting hepatic cell suspension was washed three times to remove cells with the exception of hepatic cells (at a purity greater than 95%). The hepatic cell suspension having the final density of $2.0 \times 10^6$ cells/ml was made and used for a culture experiment.

(Rate of Ammonia Removal)

Ammonia was added to a culture medium to bring the concentration to 1 mM and temporal amounts of the reduced ammonia concentration were measured to calculate a rate of ammonia removal ($\mu mol/10^6$ immobilized cells/day).

(Rate of Albumin Secretion)

Albumin secreted into the culture medium was quantified by an enzyme labeled immunoassay and converted into a rate of albumin secretion per number of initial immobilized unit cells ($\mu g/10^6$ immobilized cells/day).

Example 1

Using a polyethylene hollow fiber membrane coated with an ethylene vinyl alcohol copolymer (hereinafter, referred as to a PE/EVAL hollow fiber, 330 µm in inner diameter, 50 µm in membrane thickness) and a polypropylene hollow fiber membrane (hereinafter, referred as to a PP hollow fiber, 330 µm in inner diameter, 50 µm in membrane thickness), modified cross-section hollow fiber membranes were made by a flat plate-pressing manner shown in FIG. 2 (1). In application of a heat set by sandwiching the above hollow fiber membranes and stainless spacers, each having a thickness of 100 µm between two glass plates and leaving them to stand at 120° C. for 6 hours with the central portion of the glass plates fixed with clips, the modified cross-section hollow fiber membranes were created. The modified cross-section hollow fiber membranes that were made were denoted as PE/EVAL hollow fiber-press 100 and PP hollow fiber-press 100, respectively.

Figure 3:
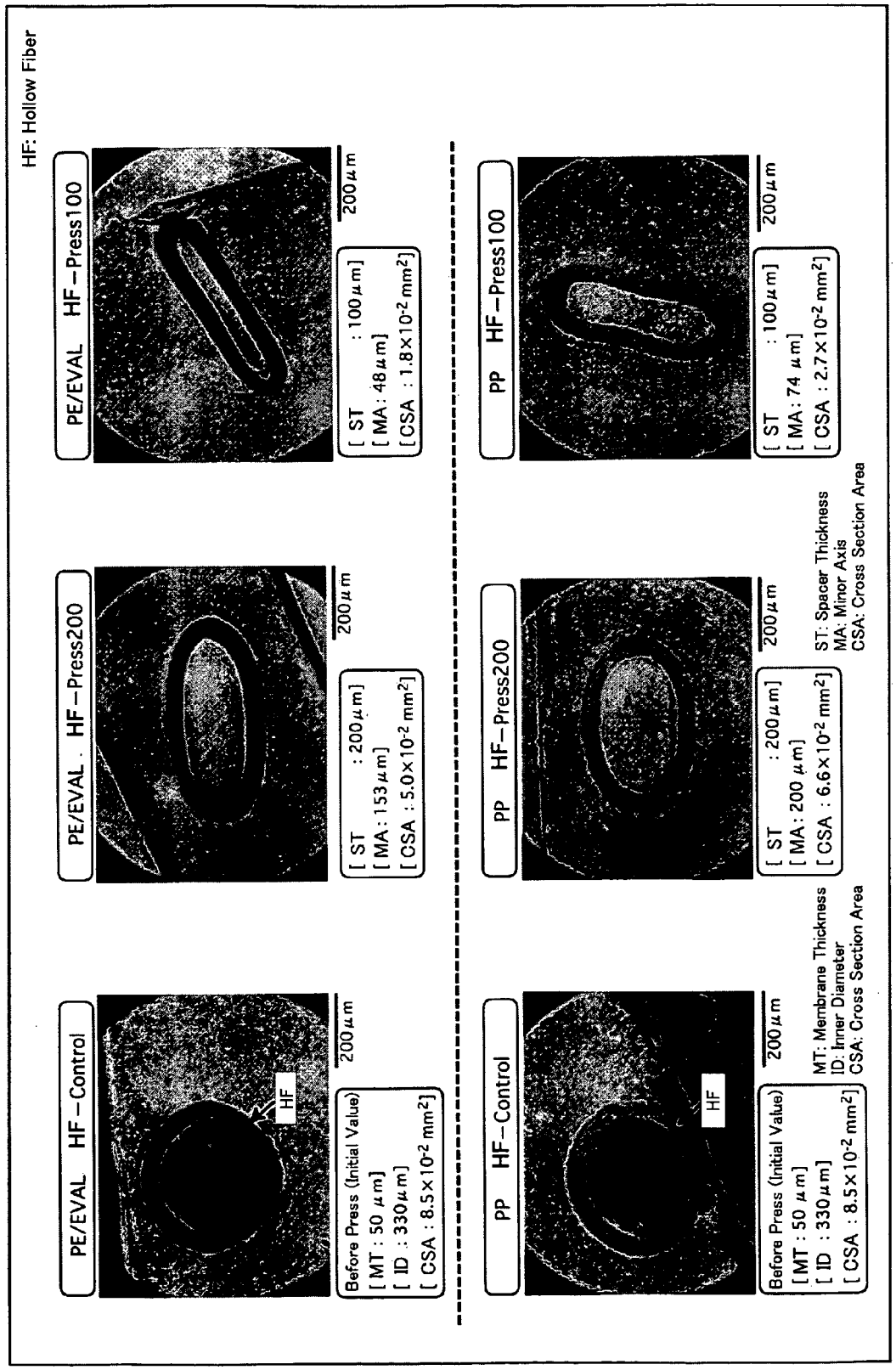
FIG. 3 is a photomicrograph showing the cross section of the modified cross-section hollow fiber membrane of the present invention.
Figure 4:
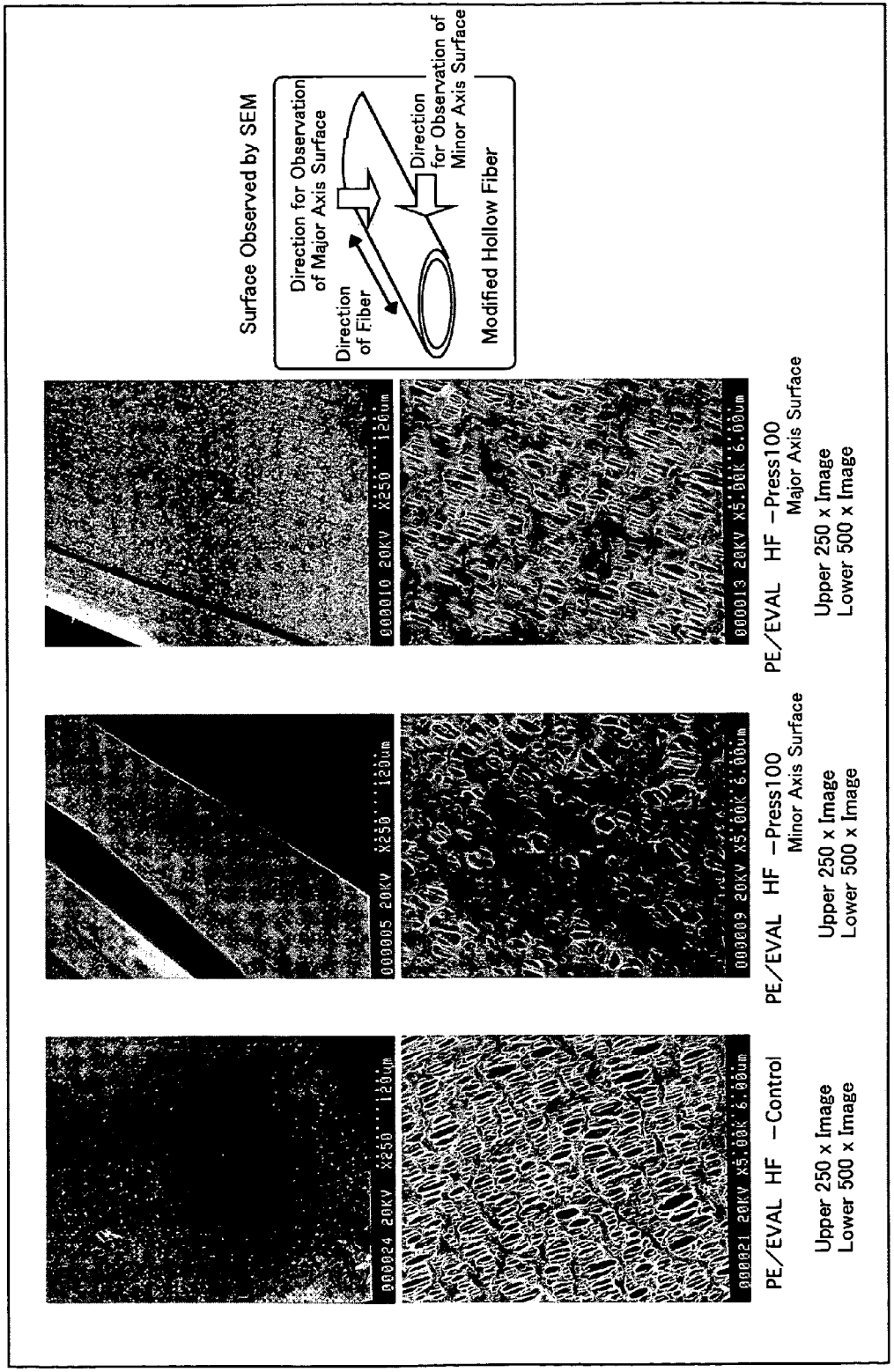
FIG. 4 is an electron photomicrograph showing the surface of a PE/EVAL modified cross-section hollow fiber membrane of the present invention.
Figure 5:
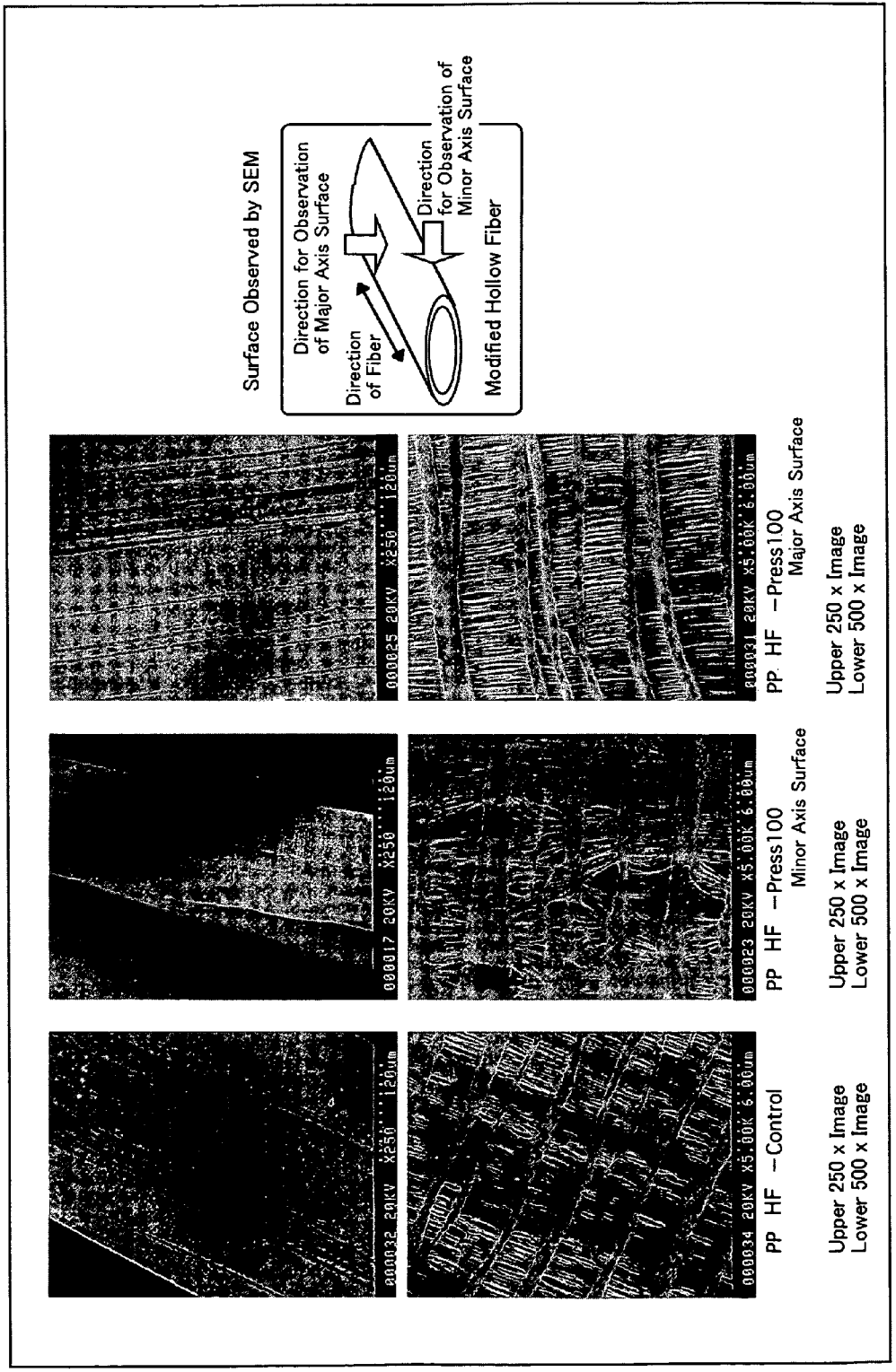
FIG. 5 is an electron photomicrograph showing the surface of a PP modified cross-section hollow fiber membrane of the present invention.

After the resulting modified cross-section hollow fiber membranes were embedded into liquid silicon, thin sections were made, thereby observing the cross-sectional shape. Moreover, using a scanning electron microscope (SEM), the surface structure of the resulting modified cross-section hollow fiber membranes was observed. The observations are shown in FIGS. 3 to 5.

Next, for the functional evaluation of a hepatic cell aggregate (organoid), made were modified cross-section hollow fiber membrane bundles of a bundle composed of nine PE/EVAL-press 100 hollow fibers each having a length of 5 cm and a bundle composed of six PP-press 100 hollow fibers each having a length of 5 cm. One end of each bundle was attached with a port for injecting cells and the other end thereof was hermetically sealed.

First, 0.6 ml of the cell suspension at $2.0 \times 10^6$ cells/ml was injected into those modified cross-section hollow fiber membrane bundles through a cell injection opening using a syringe, simultaneously by filling cells into the modified cross-section hollow fiber membranes while removing the culture solution from pores of the hollow fiber membranes by filtration. Next, in order to decrease space among the cells, high-density filling was performed by centrifugation treatment at 60×G for 90 minutes to induce the formation of the hepatic cell aggregate (organoid).

After the completion of centrifugation, the hollow fiber membranes were cut out at the position of 3 cm from the bottom end of the bundles in which the cells was filled in a very dense state, and were accommodated in a culture dish of 35 mm in diameter (manufactured by Falcon). To the culture dish, 2 ml of a serum-free medium of 13.5 g/L Dulbecco's modified eagle medium (manufactured by GIBCO) supplemented with 60 mg/L proline, 50 ng/ml EGF (manufactured by Funakoshi), 10 mg/Linsulin (manufactured by SIGMA), 7.5 mg/L hydrocortisone (manufactured by Wako Pure Chemical Industries, Ltd.), 0.1 µM copper sulfate pentahydrate (manufactured by Wako Pure Chemical Industries, Ltd.), 3 µg/L selenic acid (manufactured by Wako Pure Chemical Industries, Ltd.), 50 pM zinc sulfate heptahydrate (manufactured by Wako Pure Chemical Industries, Ltd.), 50 µg/L linoleic acid (manufactured by SIGMA), 58.8 mg/L penicillin (manufactured by Meiji Seika), 100 mg/L streptomycin (manufactured by Meiji Seika), 1.05 g/L sodium bicarbonate (manufactured by Wako Pure Chemical. Industries, Ltd.), and 1.19 g/L HEPES (manufactured by Dojindo) was added and rotation culture was performed on a shaker at 45 rpm in 5% carbon dioxide and 95% air atmosphere.

Figure 6:
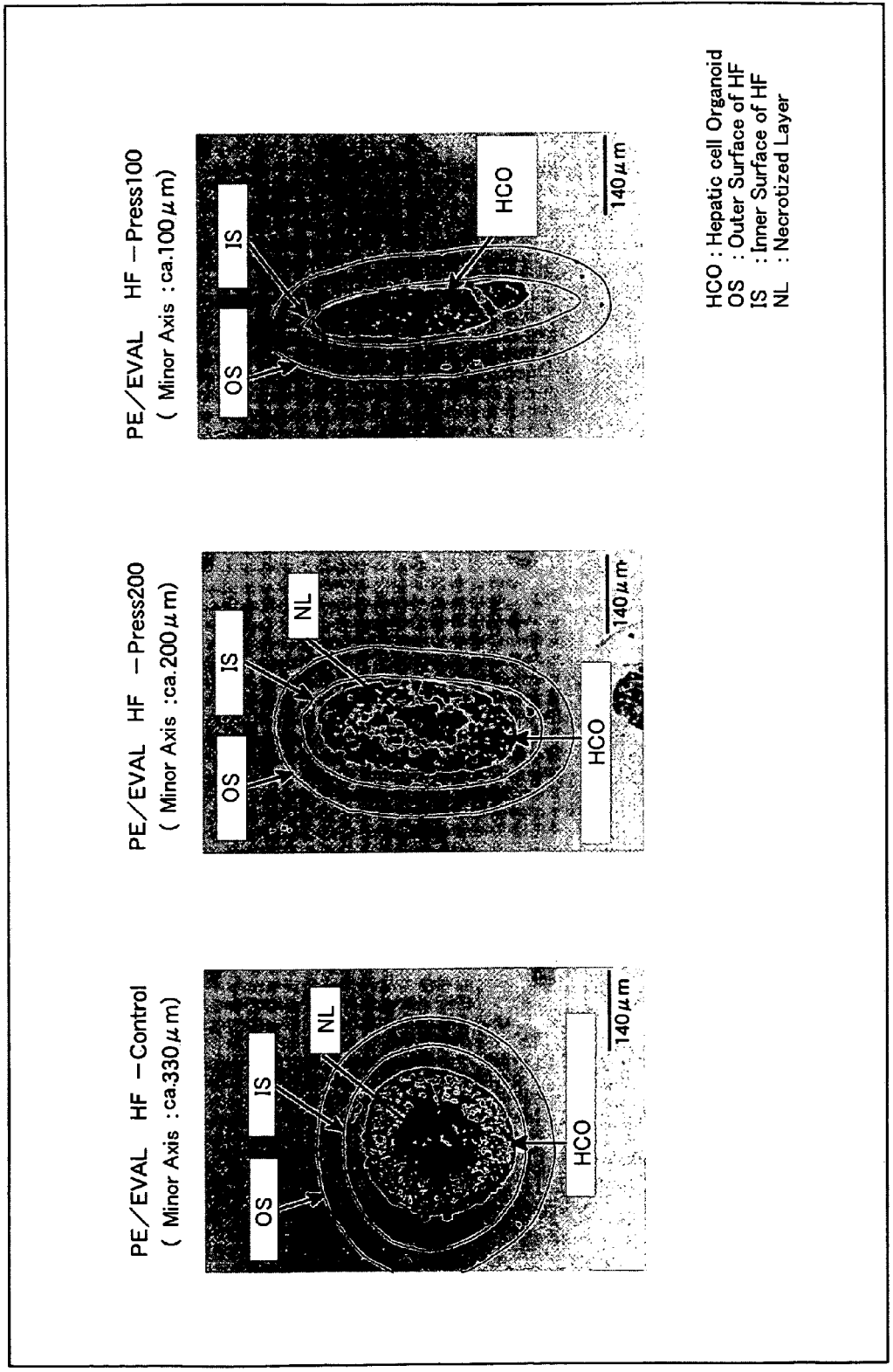
FIG. 6 is a photomicrograph showing the cross section of a cell-filled device of a modified cross-section hollow fiber membrane type of the present invention (on the 3rd day of culture, HE staining).
Figure 7:
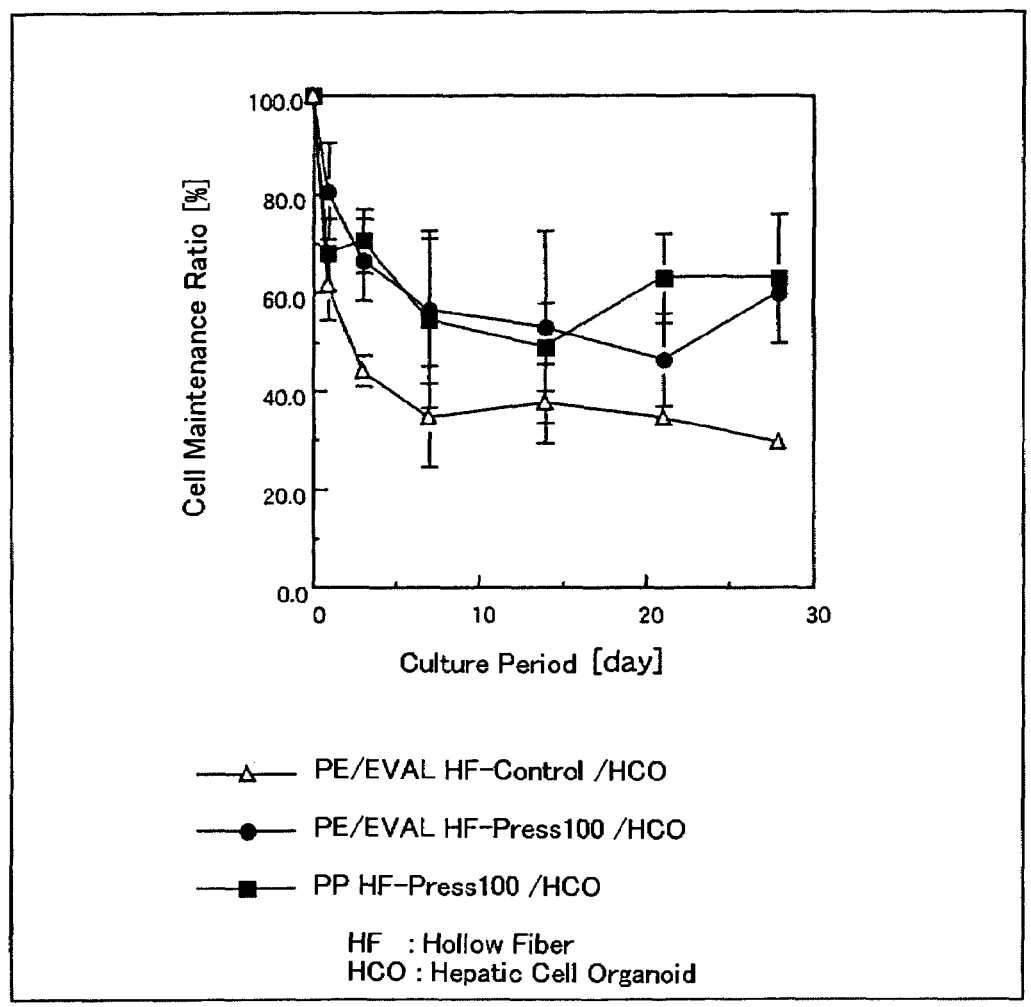
FIG. 7 is a graphical representation showing the time curve of cell maintenance ratio due to the cell-filled device of a modified cross-section hollow fiber membrane type of the present invention.

For observing the culture state of the hepatic cells, the hepatic cells filled in the hollow fiber bundles were immobilized in a 10% neutral buffered formal in solution in each period of culture. Subsequently, the immobilized hepatic cells were paraffin-embedded and thin sections were made, followed by observing the distribution of living cells and dead cells by hematoxylin-eosin staining. In addition, the hepatic cells were homoginized with a polytron homogenizer together with hollow fiber bundles in each period of culture, and nuclei leaked out therefrom were stained with crystal violet to determine the change in the number of cells by enumerating the number of nuclei. The culture state is shown in FIG. 6 and the change in the number of cells is shown in FIG. 7.

Figure 8:
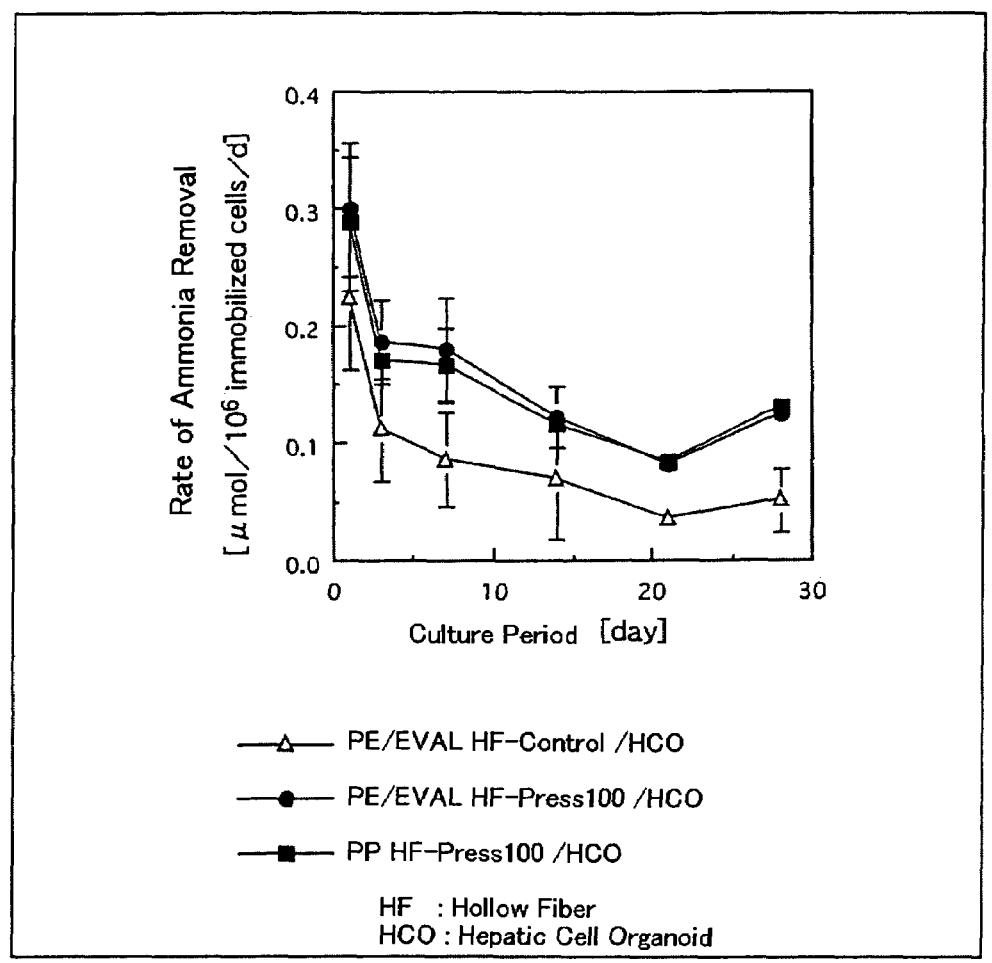
FIG. 8 is a graphical representation showing a rate of ammonia removal due to the cell-filled device of a modified cross-section hollow fiber membrane type of the present invention.
Figure 9:
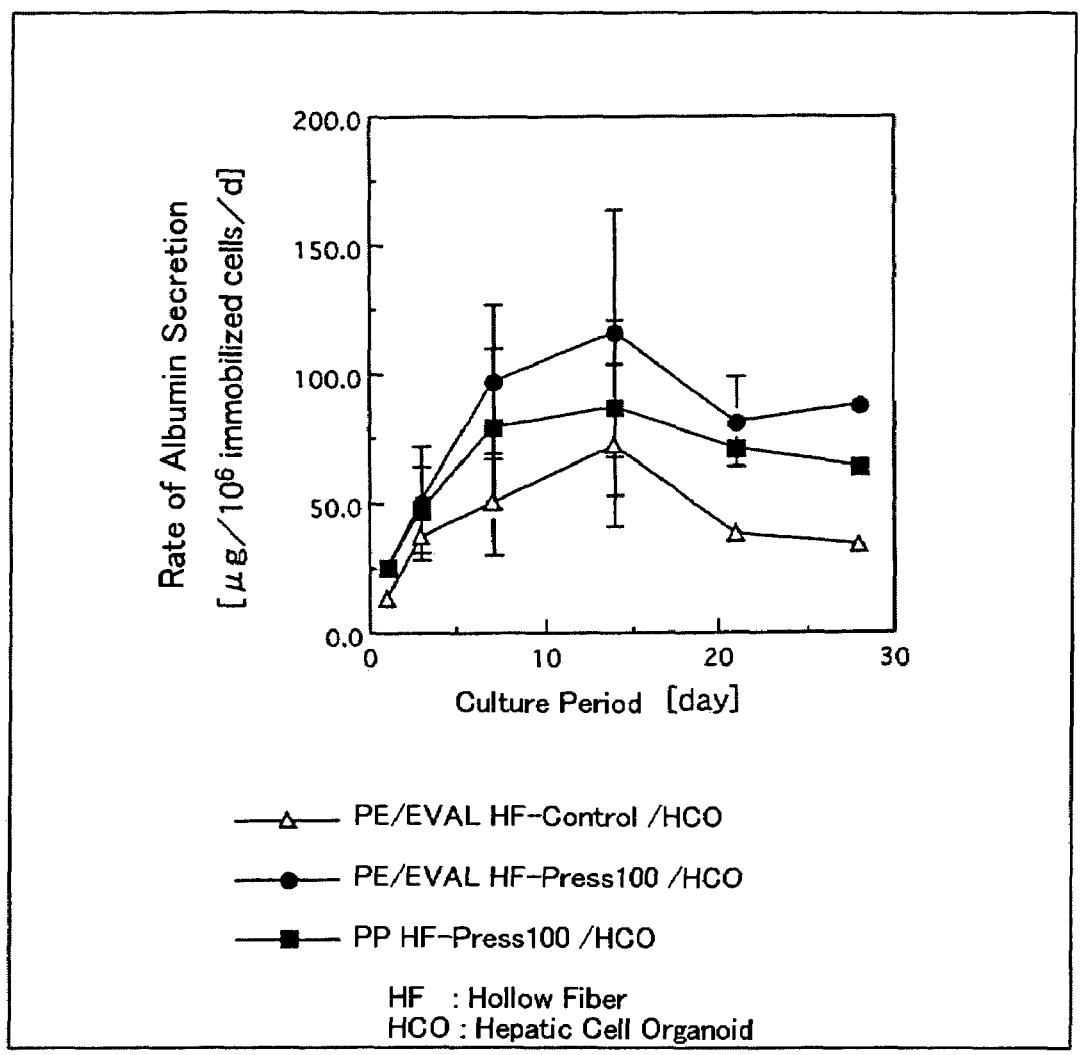
FIG. 9 is a graphical representation showing a rate of albumin secretion due to the cell-filled device of a modified cross-section hollow fiber membrane type of the present invention.

Furthermore, for the functional evaluation of the hepatic cells, ammonia was added to a culture medium to bring the concentration to 1 mM and temporal amounts of the reduced ammonia concentration were measured to evaluate their activity. Albumin secreted into the culture medium was quantified to evaluate their activity. The results are shown in FIGS. 8 and 9.

Comparative Example 1

Using a polyethylene hollow fiber membrane coated with an ethylene vinyl alcohol copolymer (hereinafter, referred as to a PE/EVAL hollow fiber Control, 330 μm in inner diameter, 50 μm in membrane thickness) and a polypropylene hollow fiber membrane (hereinafter, referred as to a PP hollow fiber Control, 330 μm in inner diameter, 50 μm in membrane thickness), a hepatic cell aggregate (organoid) was formed in the same manner as in Example 1 except that the modification processing was not carried out, to conduct the functional evaluation of hepatic cells.

Comparative Example 2

Using stainless spacers each having a thickness of 200 μm, modified cross-section hollow fiber membranes (denoted as PE/EVAL hollow fiber-press 200 and PP hollow fiber-press 200, respectively) were made. A hepatic cell aggregate (organoid) was formed in the same manner as in Example 1 except for a bundle composed of six PE/EVAL-press 200 hollow fibers each having a length of 5 cm, to conduct the functional evaluation of hepatic cells. In this Comparative Example, a modified cross section having a minor axis of 150 μm in the inner peripheral portion of the membrane, i.e., a distance from an arbitrary point of the cross section to the inner wall beyond 75 μm was obtained.

The results from the foregoing Example 1 and Comparative Examples 1 and 2 have demonstrated the following. As shown in FIG. 3 and Table 1, the modification pressing of the hollow fiber membrane produces a modified hollow fiber membrane having a minor axis of approximately 150 to 200 μm in the inner peripheral portion of the membrane by using a stainless spacer of 200 μm in thickness and a modified hollow fiber membrane having a minor axis of approximately 50 to 75 μm in the inner peripheral portion of the membrane by using a stainless spacer of 100 μm in thickness.

Moreover, as shown in FIGS. 4 and 5, in modification pressing in a pressing manner, the modification pressing was found to be well made without causing the phenomena in which pores on the hollow fiber surface, even in the most deformable site, are crushed or completely torn.

On the other hand, regarding the formation of a cell aggregate (organoid), as shown in FIG. 6, a cell aggregate (organoid) in which hepatic cells were brought into close contact with each other was formed in any of the PE/EVAL hollow fiber-Control bundle, the PE/EVAL hollow fiber-press 200 bundle, and the PE/EVAL hollow fiber-press 100 bundle. However, the PE/EVAL hollow fiber-Control bundle (Comparative Example 1) and the PE/EVAL hollow fiber-press 200 bundle (Comparative Example 2), whose hollow fibers were perfect circle-shaped and had a larger minor axis, were observed to have a dead cell layer (necrotized layer) in the central portion of the inside of the cell aggregate (organoid) likely due to the depletion of oxygen. Accordingly, it is found that the filling cells were all unable to be effectively utilized. In contrast, the PE/EVAL hollow fiber-press 100 bundle was not observed to have a necrotized layer in the central portion of the inside of the cell aggregate (organoid). As such, a minor axis of the hollow fiber is flattened to get smaller by modification pressing, and in the cross-sectional shape of a cell aggregate (organoid) formed in the hollow fiber, the distance from an arbitrary point of the cross section to the nearest inner wall of the hollow fiber is allowed to be less than 75 μm. Consequently, even for a hollow fiber membrane originally having a large inner diameter, a cell aggregate (organoid) which enables all cells to survive can be obtained by reducing an oxygen diffusion length in the cell aggregate (organoid).

For change in the number of cells, FIG. 7 shows a cell maintenance ratio which is regarded as the change in the number of cells in a hepatic cell aggregate (organoid) when the number of cells immediately after inoculating is taken as 100%. This result indicates that the number of cells can be satisfactorily maintained for a month or more in the PE/EVAL hollow fiber-press 100 bundle and the PP hollow fiber-press 100 bundle in which a necrotized layer does not occur, as compared to the PE/EVAL hollow fiber-Control bundle in which a necrotized layer occurs in the central portion.

Moreover, for the functional activity of the cell aggregate (organoid), as shown in FIGS. 8 and 9 regarding change in a rate of ammonia removal and a rate of albumin secretion per number of initial immobilized cells, the modified cross-section hollow fiber membrane bundle of the present invention maintains a better functional expression because no necrotized layer occurs in the hepatic cell aggregate (organoid).

From the above results, it is shown that the cell aggregate (organoid) using the modified cross-section hollow fiber membrane of the present invention enables the effective utilization of the filled cells without waste.

Reference Example 1

As a hollow fiber membrane, a polyethylene hollow fiber membrane to which a hydrophilic nature was imparted by coating its surface with an ethylene vinyl alcohol copolymer (hereinafter, referred as to a PE/EVAL hollow fiber, 330 μm in inner diameter, 50 μm in membrane thickness, 0.3 μm in membrane pore size) was prepared. On the other hand, as a control hollow fiber membrane, a hollow fiber membrane made of cellulose triacetate having a surface more hydrophobic than the PE/EVAL hollow fiber (hereinafter, referred as to a CTA hollow fiber, 285 μm in inner diameter, 50 μm in membrane thickness, 0.2 μm in membrane pore size) was prepared. Using each hollow fiber, hollow fiber bundles composed of six hollow fibers each having a length of 5 cm were made. One end of each bundle was connected with a port for introducing cells and the other end thereof was hermetically sealed. The filling of cells into the hollow fiber membranes and culturing of them were performed in the same manner as in Example 1 except that 0.5 ml of a cell suspension at $4.0 \times 10^6$ cells/ml was injected.

The hepatic cells filled in the hollow fiber bundles were immobilized by leaving the bundles to stand in a 10% neutral buffered formalin solution in each period of culture. Following the immobilization treatment, the hollow fibers were permeabilized to observe a cell form of the hepatic cell. Alternatively, the hollow fibers in which the hepatic cells were filled were divided in the longitudinal direction using a scalpel and the inner wall surface of the hollow fibers was exposed, followed by observation using a low vacuum scanning electron microscope.

Figure 10:
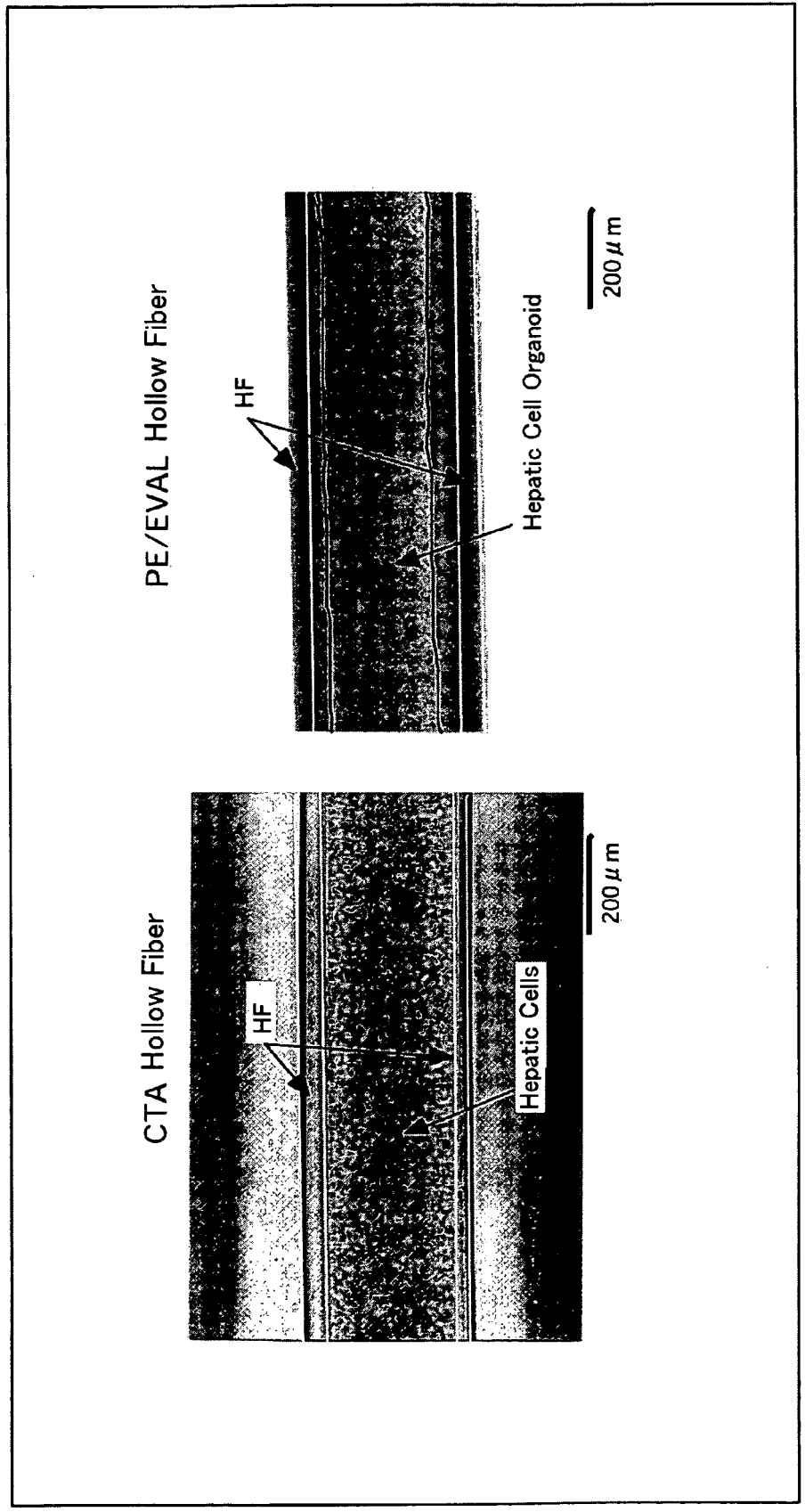
FIG. 10 is a photomicrograph showing the effects of imparting a hydrophilic nature to the surface on the formation of a cell aggregate (organoid) in the modified cross-section hollow fiber membrane of the present invention (on 1 hour of incubation).

FIG. 10 shows the cell form of the hepatic cells in the PE/EVAL hollow fiber and the CTA hollow fiber at 1 hour of culture. Thus, in the CTA hollow fiber, hepatic cells were being filled in a very dense state, but the formation of a cell aggregate (organoid) did not occur. On the other hand, in the PE/EVAL hollow fiber to which a hydrophilic nature had been imparted, a cell aggregate (organoid) was formed. Therefore, the difference in the rate of cell aggregate (organoid) formation was observed.

Figure 11:
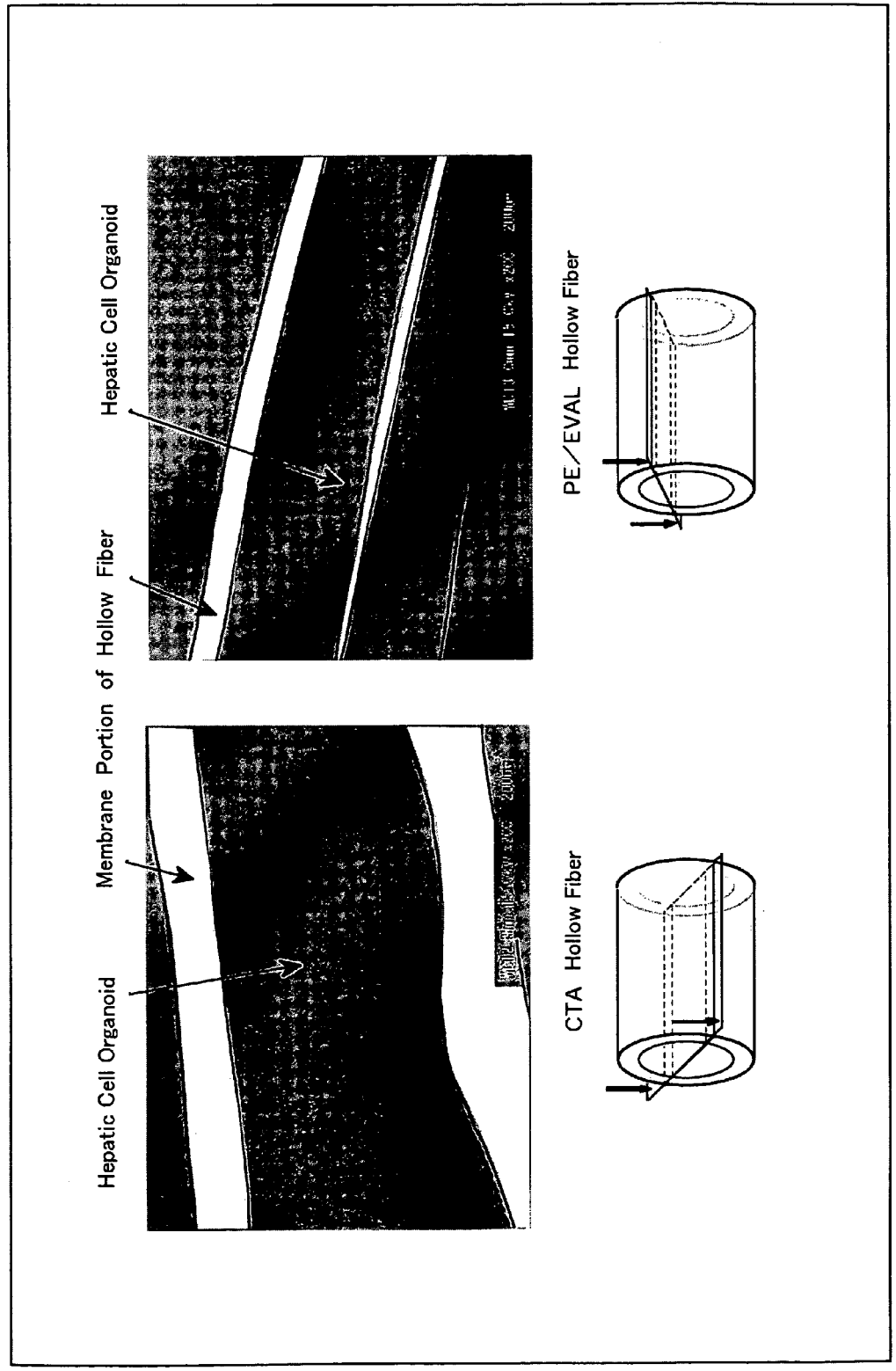
FIG. 11 is a photomicrograph showing the effects of imparting a hydrophilic nature to the surface on the cellular attachment in the modified cross-section hollow fiber membrane of the present invention (on the 1st day of incubation).

Similarly, FIG. 11 shows the states of the inner wall surface of the PE/EVAL hollow fiber and the CTA hollow fiber on the first day of culture, respectively. In the CTA hollow fiber, a cylindrical cell aggregate (organoid) was formed in the hollow fiber, although a number of hepatic cells were observed to be attached to the inner wall of the hollow fiber. On the other hand, in the PE/EVAL hollow fiber, no attachment of cells to the inner wall of the hollow fiber was observed and all hepatic cells formed a cylindrical cell aggregate (organoid).

Upon reviewing the results, the treatment of imparting a hydrophilic nature to the surface of the hollow fiber membrane suppresses the attachment of cells to the hollow fiber membrane and is effective for the early formation of a cell aggregate (organoid). In addition, the treatment is effective because the reduction in membrane permeability caused by the cellular attachment can be avoided.

The above results are summarized in Table 1.

TABLE 1

Feature of modified hollow fiber created

| Hollow fiber | Notation | Press condition | Membrane thickness [μm] | Pore size [μm] | Minor axis [μm] Before cell seeding | Minor axis [μm] After cell seeding |
|---|---|---|---|---|---|---|
| PE/EVAL hollow fiber | Control | None | 50 | 0.3 | 330 | 330 |
|  | Press200 | 200-μm spacer in use |  |  | 153 ± 22 | 214 ± 24 |
|  | Press100 | 100-μm spacer in use |  |  | 48 ± 14 | 128 ± 22 |
| PP hollow fiber | Control | None | 50 | 0.5 | 330 | 330 |
|  | Press200 | 200-μm spacer in use |  |  | 200 ± 27 | 235 ± 38 |
|  | Press100 | 100-μm spacer in use |  |  | 74 ± 18 | 147 ± 29 |

Example 2

A module having 167 elliptical modified cross-section hollow fiber membranes obtained in Example 1 (the above PP hollow fiber-press 100) filled in a housing container made of polycarbonate having a volume of 1.79 cm$^3$ was created. A schematic diagram of the created module is shown in FIG. 12. A modified cross-section hollow fiber membrane 1 was fixed within a container 2 using an urethane-based potting agent, while a sealing portion 3 for completely blocking each space at the cell injection side and at the medium perfusion side in the container 2 was formed. Furthermore, a header cap provided with a cell injection opening 4 was attached to the container 2. For performing cell seeding, the sealing portion 3 at the end of the module and the cell injection opening 4 were completely sealed in advance.

Next, primary rat hepatic cells isolated by enzyme treatment were prepared for a suspension at $4\times10^6$ cells/ml. Thereafter, 13 ml of the cell suspension was injected into the hollow portion of the modified cross-section hollow fiber membrane through the cell injection opening 4, followed by filling the cells into the hollow portion using the centrifugation condition at 60×g for 90 seconds. After the cells were filled, the cell injection opening 4 into which the cells were injected, was sealed, and the culture was performed by perfusing a culture solution through a culture solution inlet 5 and a culture solution outlet 6.

After the completion of culture, the cross section of the modified cross-section hollow fiber membrane was observed in the same manner as in Example 1. As a result, it has been shown that almost all of the rat hepatic cells filled in the hollow portions of the hollow fiber membrane survived.

Thus, in the present invention, it has been indicated that a cell aggregate (organoid) can be obtained without generating a necrotized layer, even using a hybrid artificial organ installed with a cell-filled device of a modified cross-section hollow fiber membrane type. Additionally, it is suggested that such a module have effectiveness in use for material production devices and cell incubators as well as hybrid artificial organs.

INDUSTRIAL APPLICABILITY

According to the present invention, it is shown that cells filled in a hollow fiber membrane efficiently work without waste by utilizing a hollow fiber membrane type cell-filled device. Furthermore, it is suggested that the device can be preferably utilized as an implantable or circulation type hybrid artificial organ accommodating them.

The hollow fiber membrane type cell-filled device of the present invention can be suitably used in various applications such as an implantable or circulation type hybrid artificial organ, material production devices (bioreactors) by means of cells, and cell incubators (such as stem-cell amplifiers) for growing rare cells.

The invention claimed is:

1. A cell-filled device, comprising:
   hollow fiber membranes having inner walls which define hollow portions and modified cross-sections, said cross-sections having initial shapes of perfect circles and being modified by flat plate pressing or by roller pressing to form cross-sections of deformed perfect circles; and
   a cell aggregate provided in each of the hollow portions, each cell aggregate having cells accumulated to form two or more layers in any radial direction, wherein,
   a distance from any point of the cell aggregate to the inner wall cannot be 75 μm or more.

2. The cell-filled device according to claim 1, wherein the distance to the nearest inner wall of the hollow fiber membrane is 50 μm or less.

3. The cell-filled device according to claim 1, wherein the modified cross-section hollow fiber membrane is made of a synthetic polymer having a contact angle of 70 degrees or less such that the hollow fiber membrane consists of material having a contact angle of 70 degrees or less, and the cross-section of the hollow fiber membrane is modified such that the perfect circle cross-section is deformed to an oval shape.

4. The cell-filled device according to claim 1, wherein a pore size of the hollow fiber membrane is 0.001 to 5 μm.

5. The cell-filled device according to claim 4, wherein the pore size is 0.05 to 1 μm.

6. The cell-filled device according to claim 1, wherein the hollow fiber membrane is made of a synthetic polymer having a contact angle of 70 degrees or less.

7. The cell-filled device according to claim 6, wherein synthetic polymer comprises a thermoplastic resin.

8. The cell-filled device according to claim 7, wherein the thermoplastic resin comprises a polyethylene-based resin.

9. The cell-filled device according to claim 1, wherein at least an inner surface of the hollow fiber membrane contains a hydrophilic polymer.

10. The cell-filled device according to claim 1, wherein the cells comprise cells derived from an animal tissue.

11. The cell-filled device according to claim 10, wherein the cells derived from an animal tissue comprise at least one kind of cell selected from the group consisting of cells derived from a liver, cells derived from a spleen, stem and precursor cells thereof, and genetic recombinant cells.

12. The cell-filled device according to claim 11, wherein the cells derived from an animal tissue comprise hepatic cells.

13. The cell-filled device according to claim 10, wherein the cells derived from an animal tissue comprise cells derived from a human organ.

14. A cell-filled device, comprising hollow fiber membranes and cells, provided as the cell-filled device for implantation according to claim 1, wherein each of the hollow portions contains a cell aggregate and both ends of each hollow fiber membrane are sealed.

15. The cell-filled device according to claim 1, wherein the modified cross section is a shape selected from the group consisting of a triangle, a rectangle, a parallelogram having diagonal axes of unequal length, an ellipse which is concave at the minor axis and convex at the major axis, a letter "C", and a five-pointed star.

16. The cell-filled device according to claim 15, wherein the triangle shape has concave sides.

17. The cell-filled device according to claim 15, wherein the rectangle shape has concave sides.

18. A hybrid artificial organ, comprising:
   at least one cell-filled device according to claim 1; and
   a container having an inlet and an outlet for a liquid to be treated, said container housing said at least one cell-filled device,
   wherein the hollow portions of the hollow fiber membranes of the cell-filled device provide a communication path from the inlet to the outlet for the liquid to be treated.

* * * * *

UNITED STATES PATENT AND TRADEMARK OFFICE
CERTIFICATE OF CORRECTION

PATENT NO. : 7,695,958 B2 Page 1 of 1
APPLICATION NO. : 10/525707
DATED : April 13, 2010
INVENTOR(S) : Kazumori Funatsu et al.

It is certified that error appears in the above-identified patent and that said Letters Patent is hereby corrected as shown below:

On the cover page, Item [73], the name of the assignee reading:

"Asahi Kasei Kuraray Medical Co., Ltd., Tokyo (JP)"

should be changed to:

--Asahi Kasei Kuraray Medical Co., Ltd., Tokyo (JP) and Kazumori Funatsu, Fukuoka (JP)--

Signed and Sealed this

Sixteenth Day of November, 2010

David J. Kappos
*Director of the United States Patent and Trademark Office*